(12) United States Patent
Chung

(10) Patent No.: US 12,013,398 B2
(45) Date of Patent: Jun. 18, 2024

(54) COMPOSITIONS AND METHODS FOR TREATMENT OF INVASIVE CANCERS

(71) Applicant: The George Washington University, Washington, DC (US)

(72) Inventor: Inhee Chung, Washington, DC (US)

(73) Assignee: The George Washington University, Washington, DC (US)

( * ) Notice: Subject to any disclaimer, the term of this patent is extended or adjusted under 35 U.S.C. 154(b) by 77 days.

(21) Appl. No.: 17/727,628

(22) Filed: Apr. 22, 2022

(65) Prior Publication Data

US 2022/0341937 A1   Oct. 27, 2022

Related U.S. Application Data

(60) Provisional application No. 63/178,331, filed on Apr. 22, 2021.

(51) Int. Cl.
*G01N 33/574* (2006.01)
*A61K 45/06* (2006.01)

(52) U.S. Cl.
CPC ....... *G01N 33/57492* (2013.01); *A61K 45/06* (2013.01)

(58) Field of Classification Search
CPC .. A61K 45/06; G01N 2333/705; G01N 33/53; G01N 33/532; G01N 33/533; G01N 33/574; G01N 33/57415; G01N 33/57492
See application file for complete search history.

(56) References Cited

U.S. PATENT DOCUMENTS

2014/0199330 A1* 7/2014 Lim ................. A61P 35/04
424/277.1
2017/0350895 A1  12/2017 Bremer et al.

FOREIGN PATENT DOCUMENTS

WO   WO 2010-060032 A1   5/2010
WO   WO 2017-061953 A1   4/2017

OTHER PUBLICATIONS

White, PM et. al. "TRPV4: Molecular Conductor of a Diverse Orchestra", 2016, Physiol. Rev., 96, 911-973. (Year: 2016).*
Solin, LJ et. al. "A Multigene Expression Assay to Predict Local Recurrence Risk for Ductal Carcinoma In Situ of the Breast". 2013, JNCI, 105(10), 701-710. (Year: 2013).*
Khajah, MA et. al. "Na+/K+ ATPase activity promotes invasion of endocrine resistant breast cancer cells", 2018, PLOS ONE, 13(3), 1-27. (Year: 2018).*
Parikh, U et. al. "Ductal Carcinoma In Situ: The Whole Truth", 2018, AJR, 210, 246-255. (Year: 2018).*
Solin, Lawrence J. "Management of Ductal Carcinoma In Situ (DCIS) of the Breast: Present Approaches and Future Directions", 2019, Current Oncology Reports, 21-33. (Year: 2019).*
Shan, L et. al. "Visualizing Head and Neck Tumors In Vivo Using Near-Infrared Fluorescent Transferrin Conjugate", 2008, Molecular Imaging, 7(1), 42-49. (Year: 2008).*
Cuajungco, MP et. al. "PACSINs Bind to the TRPV4 Cation Channel", 2006, JBC, 281(27), 18753-18762. (Year: 2006).*
Azimi et al., "Activation of the Ion Channel TRPV4 Induces Epithelial to Mesenchymal Transition in Breast Cancer Cells", Ira. J. Mol. Sci., Dec. 10, 2020, vol. 21, article No. 9417, pp. 1-14.
Barrio et al., "Controversies in the Treatment of Ductal Carcinoma in Situ," vol. 68:197-211, 2017.
Seijen et al., "Ductal carcinoma in situ: to treat or not to treat, that is the question," British Journal of Cancer (2019) 121:285-292.
Salvatorelli, et al., "Ductal Carcinoma In Situ of the Breast: An Update with Emphasis on Radiological and Morphological Features as Predictive Prognostic Factors," Cancers 2020, 12, 609, pp. 1-11.
Hanna, et al., "Ductal carcinoma in situ of the breast: an update for the pathologist in the era of individualized risk assessment and tailored therapies," Hanna et al., Modern Pathology (2019) 32:896-915.
Kumar et al., "Overdiagnosis and overtreatment of breast cancer, Rates of ductal carcinoma in situ: a US perspective," *Breast Cancer Research* 2005, 7:271-275.
Baxter et al., "Trends in the Treatment of Ductal Carcinoma In situ of the Breast," Journal of the National Cancer Institute, vol. 96, No. 6, Mar. 17, 2004, pp. 1-6.
Böcker, "Preneoplasia of the breast," Verh Dtsch Ges Pathol. 1997;81:502-13.
Gudjonsson et al., "Myoepithelial Cells: Their Origin and Function in Breast Morphogenesis and Neoplasia," *Journal of Mammary Gland Biology and Neoplasia*, vol. 10, No. 3, Jul. 2005, pp. 1-12.
Zhu et al., "Cancer Incidence in the U.S. Military Population: Comparison with Rates from the SEER Program," *Cancer Epidemiol Biomarkers Prev.*, Jun. 2009; 18(6): 1740-1745.
"Ductal Carcinoma In Situ (DCIS)," https://www.breastcancer.org/types/ductal-carcinoma-in-situ, downloaded Jun. 24, 2022, pp. 1-8.
Hu et al., "Regulation of In Situ to Invasive Breast Carcinoma Transition," Cancer Cell. May 2008 ; 13(5): 394-406.
Page et al., "Intraductal carcinoma of the breast: follow-up after biopsy only," Cancer. Feb. 15, 1982;49(4):751-8.
Sgroi, "Annual Review of Pathology: Mechanisms of Disease," vol. 5:193-221 (Volume publication date Feb. 2, 2010), pp. 1-5.
Chou et al., "Computer-Aided Heterogeneity Analysis in Breast Magnetic Resonance Imaging Assessment of Ductal Carcinoma in Situ: Correlating Histologic Grade and Receptor Status," *J Magn Reson Imaging*. Dec. 2017 ; 46(6): 1748-1759.

(Continued)

Primary Examiner — Nelson B Moseley, II
Assistant Examiner — Alyssa Rae Stonebraker
(74) Attorney, Agent, or Firm — Kory D. Christensen

(57) ABSTRACT

Embodiments of the instant disclosure relate to novel methods and compositions for distinguishing high-grade ductal carcinoma in situ (DCIS) from lower-grade DCIS in a breast tissue. Other embodiments of the instant disclosure provide for methods of administering one or more appropriate breast cancer treatment regimens to a subject diagnosed with high-risk DCIS.

19 Claims, 14 Drawing Sheets
(14 of 14 Drawing Sheet(s) Filed in Color)

(56) References Cited

OTHER PUBLICATIONS

Espina et al., (2010) "Malignant Precursor Cells Pre-Exist in Human Breast DCIS and Require Autophagy for Survival," PLos ONE 5(4): e10240, pp. 1-15.
Namba et al., "Heterogeneity of mammary lesions represent molecular differences," BMC Cancer 2006, 6:275, pp. 1-19.
Espina et al., "What is the malignant nature of human ductal carcinoma in situ?," Nat Rev Cancer. Jan. 2011 ; 11(1): 68-75.
Van de Vijver, "Ductal carcinoma in situ of the breast: histological classification and genetic alterations," Recent Results Cancer Res., 1998; 152:123-34.
Lester et al., "Protocol for the Examination of Specimens From Patients With Ductal Carcinoma In Situ of the Breast," Arch Pathol lab Med—vol. 133, Jan. 2009, pp. 1-11.
Sirka, "Myoepithelial cells are a dynamic barrier to epithelial dissemination," J. Cell Biol 2018 vol. 217 No. 10, 3368-3381.
Lo et al., "Tumor-associated myoepithelial cells promote the invasive progression of ductal carcinoma in situ through activation of TGFβ signaling," J. Biol. Chem. (2017) 292(27) 11466-11484.
Nelson et al., "Breaking Through to the Other Side: Microenvironment Contributions to DCIS Initiation and Progression," J Mammary Gland Biol Neoplasia. Dec. 2018 ; 23(4): 207-221.
Veeck et al., "Breast Cancer Epigenetics: From DNA Methylation to microRNAs," J Mammary Gland Bio Neoplasia (2010) 15:5-17.
Wei et al, "Matrix stiffness drives Epithelial-Mesenchymal Transition and tumour metastasis through a TWIST1-G3BP2 mechanotransduction pathway," Nat Cell Biol. May 2015 ; 17(5):678-688.
Veeck et al., "Breast Cancer Epigenetics: From DNA Methylation to micro RNAs," J Mammary Grand Biol Neoplasia (2010) 15:5-17.
Hu et al., "Distinct epigenetic changes in the stromal cells of breast cancers," Nature Genetics, vol. 37, No. 8, Aug. 2005, pp. 1-7.
So et al., "Differential Expression of Key Signaling Proteins in MCF10 Cell Lines, a Human Breast Cancer Progression Model," Mol Cell Pharmacol.; 4(1): 31-40.
Miller et el., "MCF10DCIS.com Xenograft Model of Human Comedo Ductal Carcinoma In Situ," Journal of the National Cancer Institute, vol. 92, No. 14, Jul. 19, 2000, pp. 1185-1186.
Liu et al., "Microfluidic cytometric analysis of cancer cell transportability and invasiveness," Scientific Reports 5:14272, 2015, pp. 2-12.
Dai et al., "Breast Cancer Cell Line Classification and Its Relevance with Breast Tumor Subtyping," Journal of Cancer, 2017; 8(16): 3131-3141.
Weinberg, "Determinants of Invasion and Metastasis," Medicina (Buenos Aires), 2007: 67 (Supp. II): 3-5.
Swaminathan et al., "Mechanical stiffness grades metastatic potential in patient tumor cells and in cancer cell lines," Cancer Res. Aug. 1, 2011; 71(15): 5075-5080, pp. 5-18.
Han et al., "Cell swelling, softening and invasion in a three-dimensional breast cancer model," Nature Physics, vol. 16, Jan. 2020, 101-108.
Watkins et al., "Hydrodynamic Cellular Volume Changes Enable Glioma Cell Invasion," J. Neuroci., Nov. 23, 2011, 31(47): 17250-17259.
Gkrestsi et al., "Cell Adhesion and Matrix Stiffness: Coordination Cancer Cell Invasion and Metastasis," Frontiers in Oncology, May 2018, vol. 8, Article 145, pp. 1-7.
Guo, et al., "Cell volume change through water efflux impacts cell stiffness and stem cell fate," PNAS, published online Sep. 25, 2017, downloaded from https://www.pnas.org on Jun. 24, 2022, pp. 1-10.
Guo, M., et al. (2017). Cell volume change through water efflux impacts cell stiffness and stem cell fate. Proceedings of the National Academy of Sciences of the United States of America 114, E8618-E8627.
Lang et al., "Functional Significance of Cell Volume Regulatory Mechanisms," Physiological Reviews, vol. 78, No. 1, Jan. 1998, pp. 1-60.
Tzur, et al., "Cell Growth and Homeostasis in Proliferating Animal Cells," Science Jul. 10, 2009, vol. 325, issue 5937, pp. 167-171.

Yang et al., "TRPV4 activates the Cdc42/N-wasp pathway to promote glioblastoma invasion by altering cellular protrusions," Scientic Reporrts (2020) 10:14151, pp. 1-15.
Zhou et al., "Membrane potential modulates plasma membrane phospholipid dynamics and K-Ras signaling," Science, Aug. 21, 2015; 349(6250): 853-876.
Willis, "Targeted Cancer Therapy: Vital Oncogenes and a New Molecular Genetic Paradigm for Cancer Initiation Progression and Treatment," Int. J. Mol. Sci, 2016, 17, 1552, pp. 1-23.
Gross et al., "Targeting cancer with kinase inhibitors," the Journal of Clinical Investigation, vol. 125, No. 5, May 2015, pp. 1-10.
Hoffmann, Ion Channels Involved in Cell Volume Regulation: Effects on Migration, Proliferation, and Programmed Cell Death in Non Adherent EAT shells and Adherent ELA Cells, Cell Physiol Biochem 2011;28:1061-1078, pp. 1-18.
Alevizopoulos, K., et al. (2014). Na+/K+ ATPase Inhibitors in Cancer. Current Drug Targets 15, 988-1000.
Baratchi et al., "The TRPV4 Agonist GSK1016790A Regulates the membrane Expression of TRPV4 Channels," Frontiers in Pharmacology, Jan. 2019, vol. 10, Article 6, pp. 1-12.
Liu et al., "Activation of PTEM by inhibition of TRPV4 suppresses colon cancer development" Cell Death and Disease (2019) 10:460, pp. 1-14.
Casey et al., "3D hydrogel-based microwell arrays as a tumor microenvironment model to study breast cancer growth," 2017 Biomed. Mater. 12 025009, pp. 1-13.
Kontomaris et at., "Hertz model or Oliver & Pharr analysis? Tutorial regarding AFM nanoindentation experiments on biological samples," 2020 Mater. Res. Express 7 033001, pp. 1-13.
Chao et al., "Cytoskeletal Contribution to Cell Stiffness Due to Osmotic Swelling; Extending the Donnan Equilibrium," vol. 81, 2018, pp. 83-96.
Zhou et al., "Universal behavior of the osmotically compressed cell and its analogy to the colloidal glass transition," 10632-10637, PNAS, Jun. 30, 2009, vol. 106, No. 26.
Denisin et al., "Tuning the Range of Polyacrylamide Gel Stiffness for Mechanobiology Applications," ACS Appl. Mater. Interfaces, 2016, 8,34, 21893-21902.
Fischer et al., "Stiffness-controlled three-dimensional extracellular matrices for high-resolution imaging of cell behavior," Nature Protocols, vol. 7 No. 11, 2012, pp. 2056-2066.
Lee et al., "YAP-independent mechanotransduction drives breast cancer progression," Nature Communicatons, (2019)10:1848, pp. 1-9.
Paszek et al., "Tensional homeostasis and the malignant phenotype," Cancer Cell : Sep. 2005, vol. 8, pp. 241-254.
Provenzano et al., "Collagen density promotes mammary tumor initiation and progression," BMC Medicine 2008, 6:11, pp. 1741-7015.
Chaudhuri et al., "Extracellular matrix stiffness and composition jointly regulate the induction of malignant phenotypes in mammary epithelium," Nature Materials, vol. 13, Oct. 2014, pp. 970-978.
Venugopal et al., Cell density overrides the effect of substrate stiffness on human mesenchymal stem cells' morphology and proliferation, Biomater Sci, 2018, 6, 1109-1119.
Recasens et al., "Targeting Cancer Cell Dormancy," Review, vol. 40, Issue 2, p. 128-141, Feb. 1, 2019.
Aguirre-Ghiso, "Models, mechanisms and clinical evidence for cancer dormancy," Nat Rev Cancer, Nov. 2007 ; 7(11): 834-846.
Ma et al., "Trichostatin A, a histone deacetylase inhibitor, suppresses proliferation and promotes apoptosis of esophageal squamous cell lines," Molecular Medicine Reports, 11: 4525-4531, 2015.
Debnath, et al., "Morphogenesis and oncogenesis of MCF-10A mammary epithelial acini grown in three-dimensional basement membrane cultures," Methods. Jul. 2003;30(3):256-68.
Robinson et al., "Quantitative analysis of 3D extracellular matrix remodelling by pancreatic stellate cells," Biology Open (2016) 5, 875-882.
Gustafsson et al., "Structured-illumination microscopy of living cells," (2009), Abstracts of Papers of the American Chemical Society, 238.

(56) References Cited

OTHER PUBLICATIONS

Shao et al., "Super-resolution 3D microscopy of live whole cells using structured illumination," vol. 8, No. 12, Dec. 2011, Nature Methods.

Gustafsson et al., "Three-Dimensional Resolution Doubling in Wide-Field Fluorescence Microscopy by Structured Illumination," Biophysical Journal, vol. 94, Jun. 2008, 4957-4970.

Sekharam et al., "Insulin-like Growth Factor 1 Receptor Enhances Invasion and Induces Resistance to Apoptosis of Colon Cancer Cells through the Akt/Bcl-$X_L$ Pathway," Cancer Research 63, 7708-7716, Nov. 15, 2003.

Yu et al., "Transient receptor potential ion-channel subfamily V member 4: a potential target for cancer treatment," *Cell Death and Disease* (2019)10:497, pp. 1-17.

Veys et al., "Quantitative single-cell ion-channel gene expression profiling through an improved qRT-PCR technique combined with whole cell patch clamp," Journal of Neuroscience Methods 209 (2012) 227-234.

Seltmann et al., "Keratins significantly contribute to cell stiffness and impact invasive behavior," PNAS, Nov. 12, 2013, vol. 110, No. 46, 18507-18512.

Zhao, et al., "Vimentin affects the mobility and invasiveness of prostate cancer cells," Cell Biochem Funct., Sep.-Oct. 2008;26(5):571-7.

Lang, F. et al., "Ion channels and cell volume in regulation of cell proliferation and apoptotic cell death," Contrib Nephrol, vol. 152, pp. 142-160. (2006).

Lee, W.H. et al., "TRPV4 plays a role in breast cancer cell migration via Ca2+-dependent activation of AKT and downregulation of E-cadherin cell cortex protein," Oncogenesis (2017), vol. 6, 12 pages.

\* cited by examiner

Fig. 3A
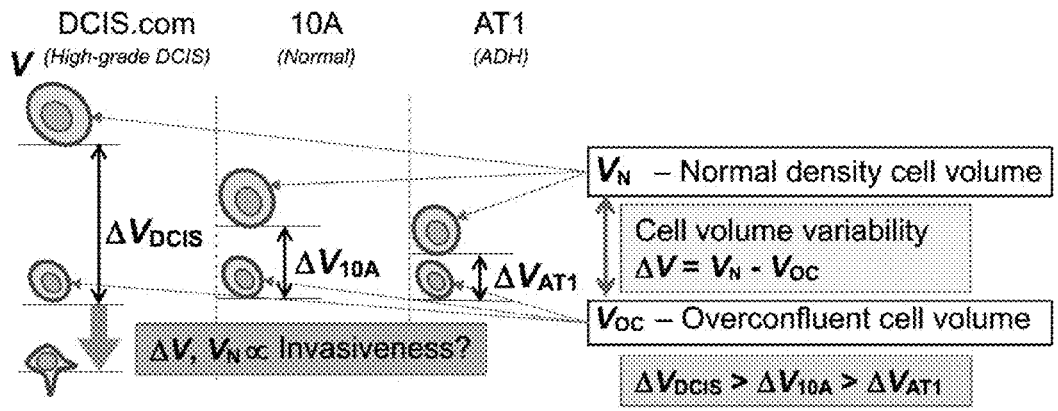
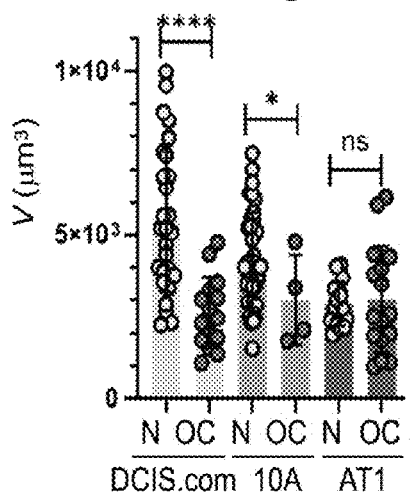
Fig. 3B
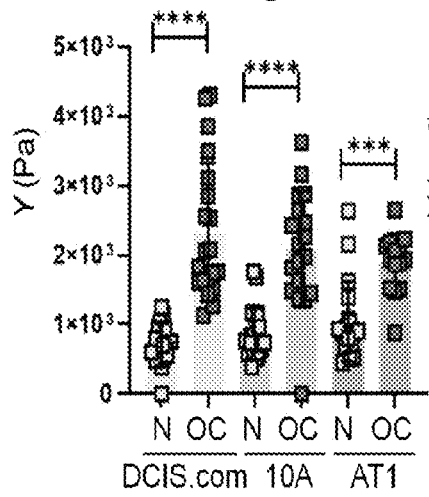
Fig. 3C
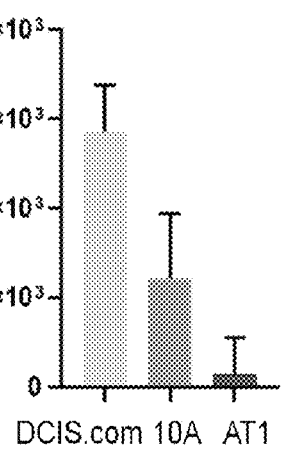
Fig. 3D

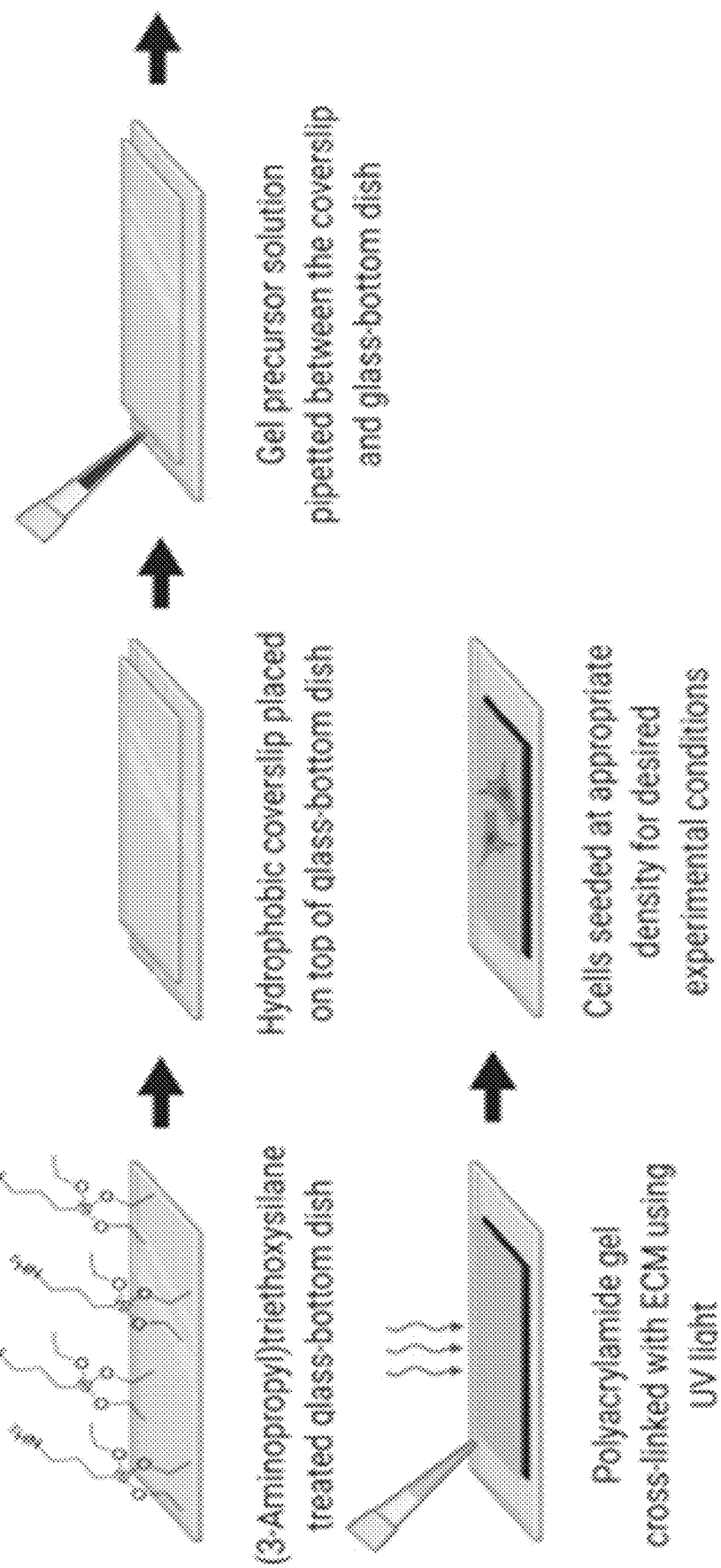

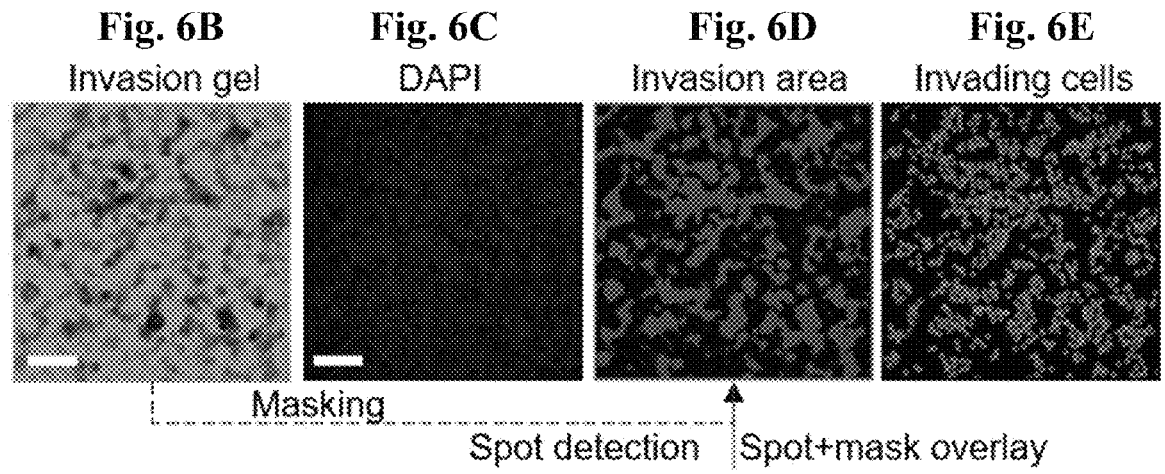
Fig. 6B Invasion gel | Fig. 6C DAPI | Fig. 6D Invasion area | Fig. 6E Invading cells
Masking — Spot detection — Spot+mask overlay
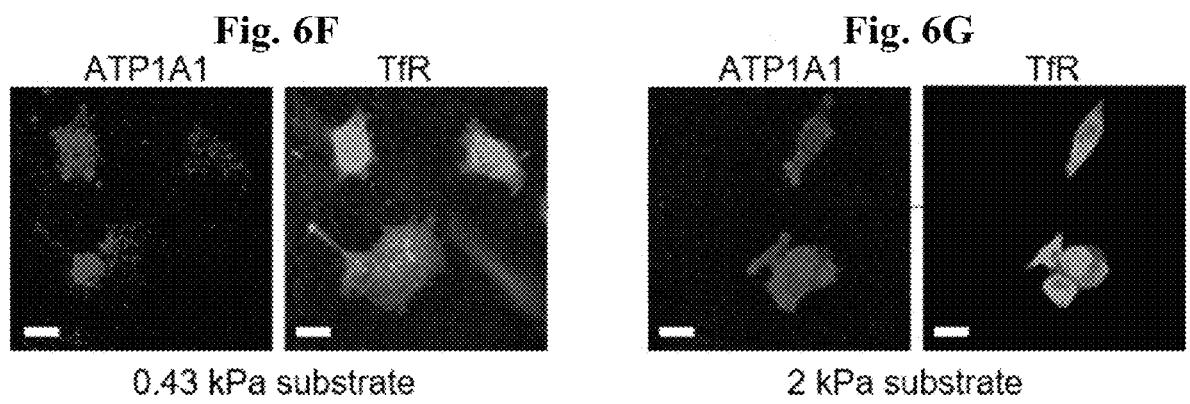
Fig. 6F ATP1A1 | TfR
0.43 kPa substrate
Fig. 6G ATP1A1 | TfR
2 kPa substrate

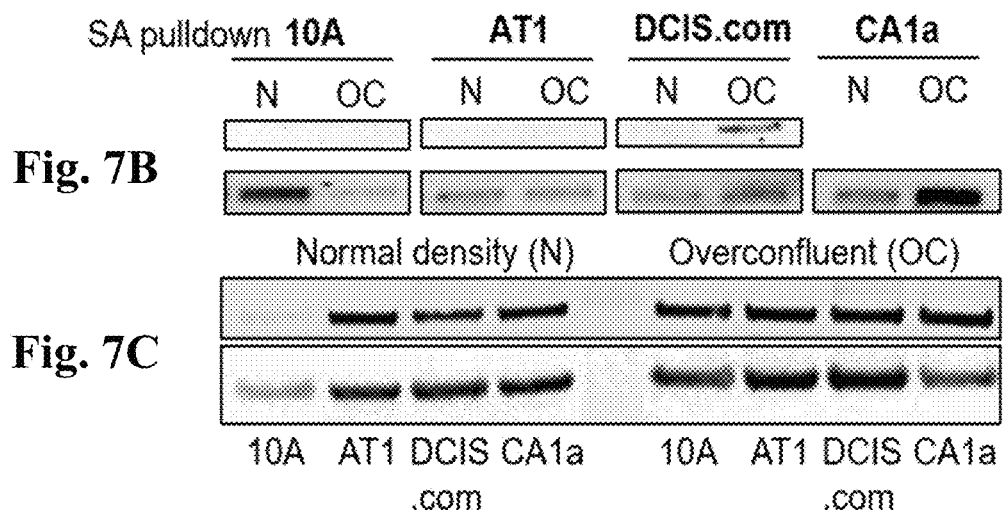
Fig. 7B
Fig. 7C
Fig. 7D
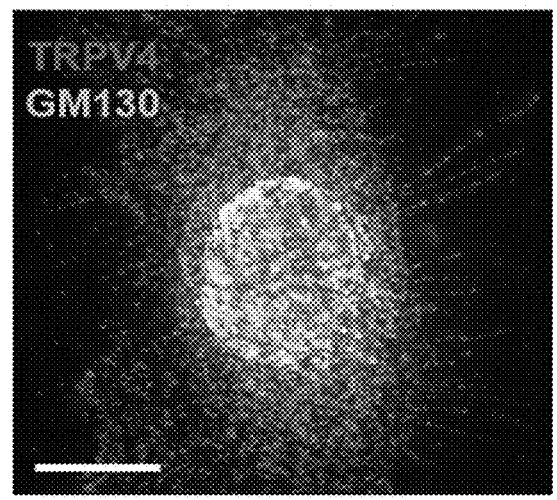

Normal

Benign

ADH

IMG-DCIS

HG-DCIS

IDC

Fig. 10A
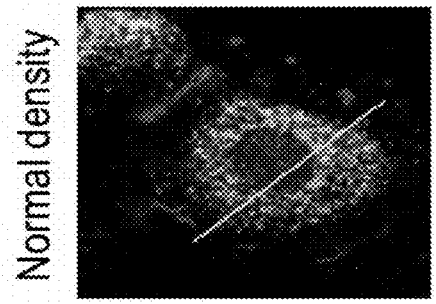 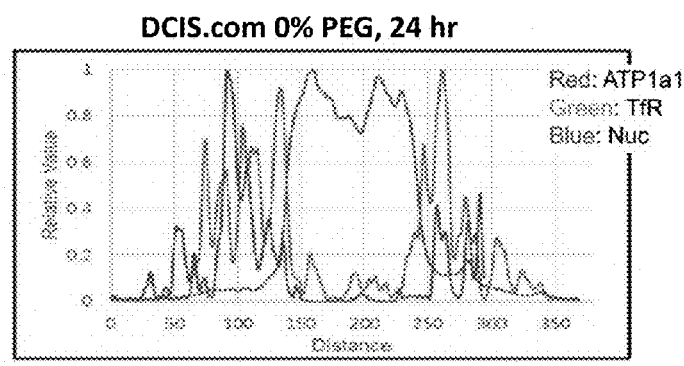
Fig. 10B
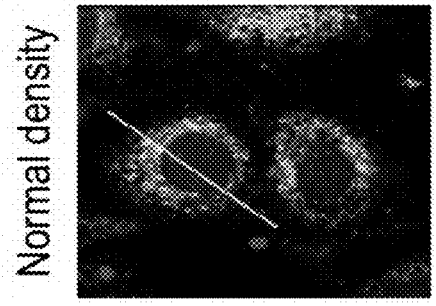 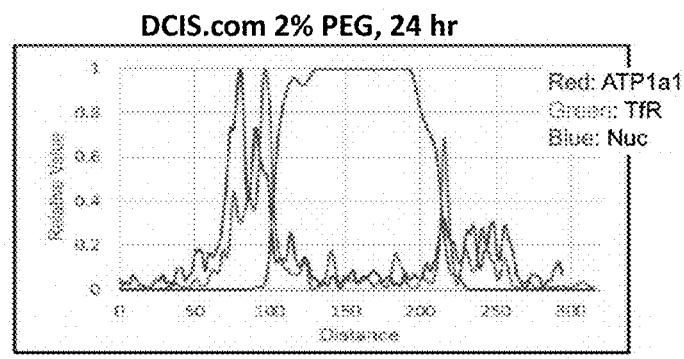
Fig. 10C
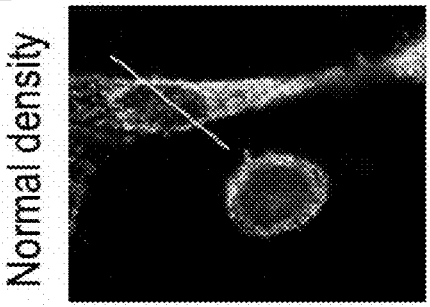 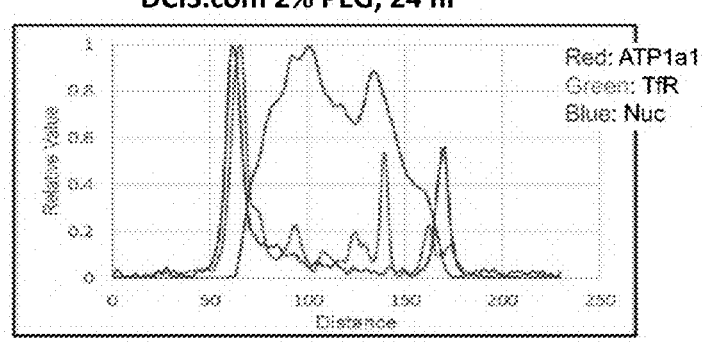
Fig. 10D
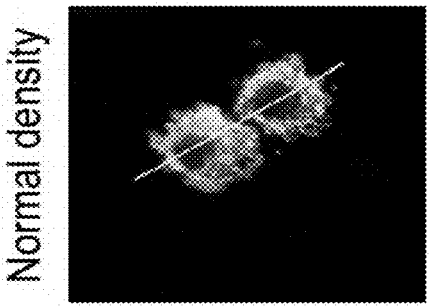 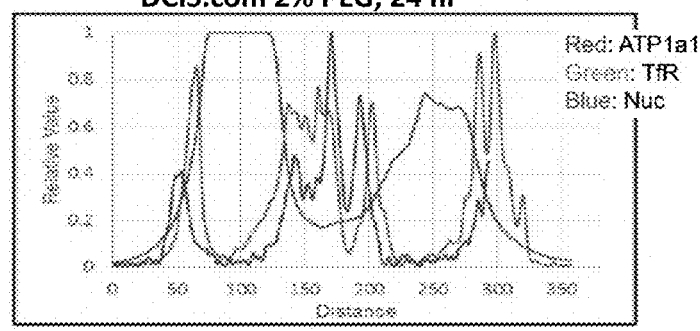

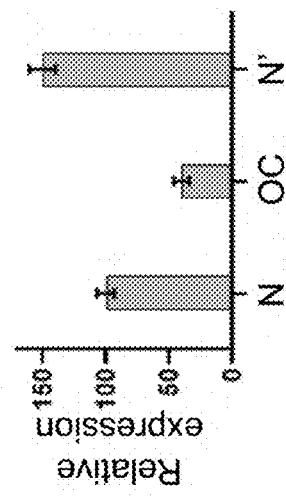
Fig. 11A
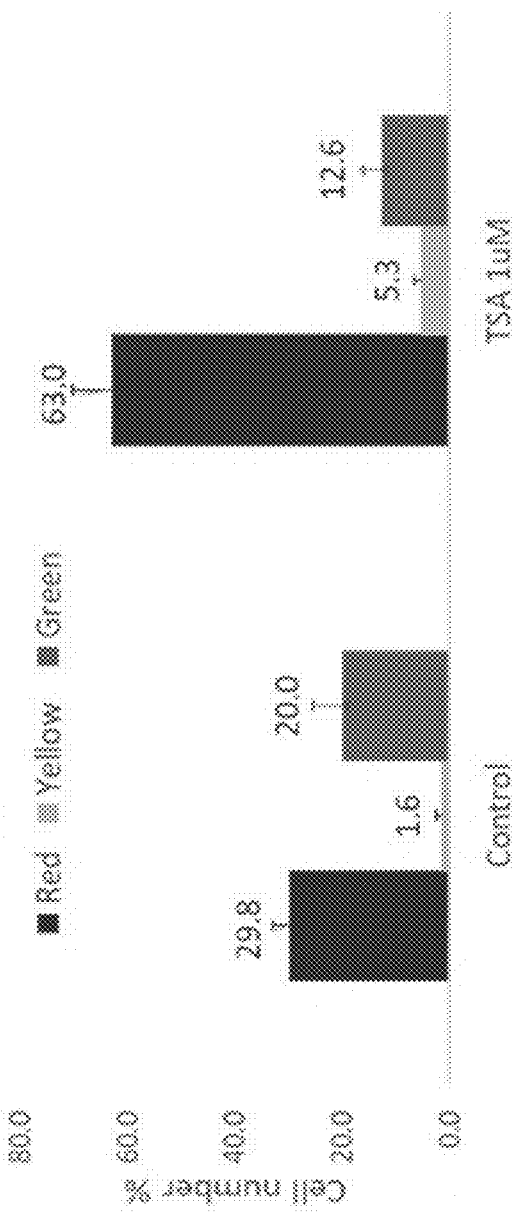
Fig. 11B
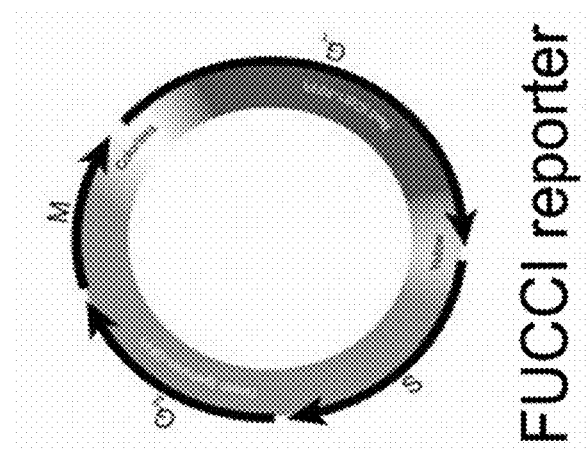

COMPOSITIONS AND METHODS FOR TREATMENT OF INVASIVE CANCERS

CROSS REFERENCE TO RELATED APPLICATION

This application claims the benefit of U.S. Provisional Application No. 63/178,331, filed on Apr. 22, 2021, the disclosure of which is hereby incorporated by reference in its entirety.

FIELD

Embodiments of the instant disclosure relate to novel methods and compositions for diagnosing and/or monitoring cancer in a subject having or suspected of having cancer. In certain embodiments, methods and compositions disclosed herein may be used to diagnose a cancer, characterize a cancer, determine a cancer prognosis, predict the outcome of a cancer therapy, and any combination thereof.

BACKGROUND

Diagnosing, monitoring, and treating cancer is currently a pressing health issue. Of all cancers, breast cancer is the most common cancer in women, and breast cancer-related deaths are second only to lung cancer in the United States. Although aggressive care for treating breast cancer can be warranted in some patients, there remains a frequent problem with overdiagnosis and overtreatment for those diagnosed with ductal carcinoma in situ (DCIS). This pre-invasive form of breast cancer develops within the breast duct and accounts for approximately 20% of newly diagnosed breast cancer cases each year. More than half of DCIS cases do not progress to invasive cancer. Nonetheless, patients with DCIS typically undergo aggressive treatment such as surgery and radiation. This causes tens of thousands of patients each year to experience unnecessary anxiety and significant physical discomfort. This aggressive approach reflects the lack of clinical tools available to determine which patients might benefit from aggressive procedures, which stems from the limited knowledge of DCIS pathogenesis in the field. As such, there is a need for compositions and methods of using such compositions for determining the risk of invasive cancer progression of DCIS.

SUMMARY

The present disclosure is based, at least in part, on the novel discovery of single-cell level determinants of invasive transition of DCIS cells and that these determinants can be leveraged as diagnostic markers. The present disclosure provides molecular markers unknown to the field that can predict the risk of progression of DCIS to invasive ductal cancer (IDC) and are not confounded by the broad heterogeneity of DCIS samples which currently limits the clinical use of other genetic and/or epigenetic markers known in the field.

Embodiments of the present disclosure provide methods of treating breast cancer in a subject in need thereof. In some aspects, a subject in need thereof may have, or be suspected of having at least one breast tissue abnormality. In certain embodiments, the present disclosure provides methods and compositions that may be used to identify a breast tissue abnormality as a precursor to breast cancer in a subject in need thereof. In some embodiments, the present disclosure provides methods for treating breast cancer. Methods for treating breast cancer disclosed herein may comprise: i) identifying at least one precursor to breast cancer in a subject, wherein identification of the at least one precursor to breast cancer comprises collecting a tissue sample from a breast tissue abnormality in the subject, and identifying the at least one precursor to breast cancer in the subject as wherein one or more cells in the tissue sample has one or more ion channels localized at the plasma membrane; and ii) treating the subject having the at least one precursor to breast cancer by administering chemotherapy to said subject, administering radiation to said subject, surgically removing breast tissue, applying a targeted therapy, or a combination thereof. In some embodiments, methods of treating breast cancer disclosed herein may comprise selecting a subject with DCIS, said subject having provided a tissue sample having the presence of one or more ion channels localized at the plasma membrane that is indicative of a DCIS with a high likelihood of becoming invasive; and treating said subject for high-grade DCIS comprising administering chemotherapy to said subject, administering radiation to said subject, surgically removing breast tissue, applying a targeted therapy, or a combination thereof.

In certain embodiments, the present disclosure provides methods of treating DCIS in a subject in need thereof. In some aspects, a subject in need thereof may have, or be suspected of having DCIS. In some embodiments, methods of treating DCIS disclosed herein may comprise selecting a subject with DCIS, said subject having provided a tissue sample having the presence of one or more ion channels localized at the plasma membrane that is indicative of a DCIS with a high likelihood of becoming invasive; and treating said subject for DCIS comprising administering chemotherapy to said subject, administering radiation to said subject, surgically removing breast tissue, applying a targeted therapy, or a combination thereof. In some embodiments, one or more ion channels are not localized at the plasma membrane in all of the DCIS cells in a tissue sample from a subject identified as having ductal carcinoma in situ but are localized at the plasma membrane in some of the DCIS cells in such a tissue sample. In some embodiments, one or more ion channels can be selected from the group consisting of TRPV4 and ATP1A1.

In certain embodiments, the presence of one or more ion channels localized at the plasma membrane may be determined by a process comprising the steps of: obtaining a biological sample from said subject; and detecting the presence of one or more ion channels localized at the plasma membrane of cells in the biological sample. In some aspects, methods of detecting the presence of one or more ion channels localized at the plasma membrane of cells may comprise detecting the presence of at least two ion channels localized at the plasma membrane.

In some embodiments, methods of detecting the presence of one or more ion channels localized at the plasma membrane of cells may further comprise calculating an invasiveness risk score from said presence of said one or more ion channels localized at the plasma membrane. In some aspects, an invasiveness risk score can be calculated herein by either quantifying the fraction of ductal carcinoma in situ cells in the tissue sample that have a presence of one or more ion channels localized at the plasma membrane or by quantitatively assessing the level of said presence in each positive ductal carcinoma in situ cell in the tissue sample wherein a higher fraction or higher level correlates with a high invasiveness risk. In some aspects, methods of qualitative assessment may comprise using a multivariate prediction model to determine if a pattern of plasma membrane localization of one or more ion channels is indicative of a DCIS with high risk of becoming invasive.

In some embodiments, methods of the present disclosure may be performed on a biological sample collected from the subject. In some aspects, a biological sample may be a breast tissue sample. In some other aspects, a biological sample may be a breast tissue sample from a breast tissue abnormality.

In some embodiments, methods disclosed herein of detecting the presence of one or more ion channels localized at the plasma membrane may comprise immunohistochemistry, immunocytochemistry, flow cytometry, or any combination thereof. In some aspects, methods disclosed herein may use antibodies or antibody fragments that bind to one or more ion channels of interest. In some other aspects, to enable detection, either the antibodies or antibody fragments that bind to one or more ion channels of interest can be directly labeled with a label. In some aspects, the label may be a fluorescent marker or with an enzyme, a small molecule such as biotin that is the target of a binding protein, and/or a contrast agent such as nanoparticles. In some aspects, methods disclosed herein may further comprise a second antibody that binds to the antibodies or antibody fragments that bind to the one or more ion channels, wherein said second antibody can be labelled with a label disclosed herein.

In some embodiments, the presence of one or more ion channels localized at the plasma membrane as determined according to the methods disclosed herein, may be confirmed by comparison with at least one invariant control marker present at the plasma membrane. In some aspects, an invariant control marker is a transferrin receptor.

In some embodiments, methods of treatment disclosed herein may treat ductal carcinoma in situ. In some embodiments, methods of treatment disclosed herein may treat a breast abnormality or pathology that has previously been identified as ductal carcinoma in situ by calcification detected by mammography.

In some embodiments, the presence of the one or more ion channels localized at the plasma membrane can be determined by comparing a signal corresponding to the plasma membrane localization level of the one or more ion channels to either or both of the level or levels of a signal corresponding to cytoplasmic localization of the one or more ion channels and a signal corresponding to nuclear localization of the one or more ion channels. In some aspects, the localization of the one or more ion channels may be confirmed by colocation with one or more invariant control proteins or DNA markers of one or more of the plasma membrane, cytoplasm, or nucleus.

In certain embodiments, the present disclosure provides kits for use in performing any of the methods disclosed herein. In some embodiments, kits disclosed herein may be used in identifying a breast tissue abnormality as a precursor to breast cancer in a subject in need thereof. In some embodiments, kits disclosed herein may be used in diagnosing a likelihood of DCIS becoming invasive in a subject. In some embodiments, kits disclosed herein may comprise one or more of the following: a plurality of agents that specifically bind one or more ion channels, wherein said one or more ion channels are localized at the plasma membrane selectively in ductal carcinoma in situ cells having a high likelihood of becoming invasive; an agent that specifically binds to at least one invariant plasma membrane control marker; a container for housing said plurality of agents and said agent; and/or instructions for use of said plurality of agents and said agent for determining an increase in the plasma membrane localization of said one or more ion channels by comparing the plasma membrane localization of said one or more ion channels to said at least one invariant control plasma membrane marker wherein an increase in the level of plasma membrane localization of said one or more ion channels as compared to the at least one invariant control plasma membrane marker is indicative of a breast cancer with a high likelihood of becoming invasive. In some aspects, the one or more ion channels may be TRPV4 and/or ATP1A1.

In some embodiments, kits disclosed herein may comprise plurality of agents, wherein the agents can be antibodies that specifically bind to plasma membrane localized ion channel proteins and plasma membrane localized proteins of the at least one invariant control plasma membrane marker. In some aspects, the antibodies may be labeled with at least one detectable marker. In some embodiments, kits disclosed herein may comprise agents that can specifically bind to one or more ion channels bind to ion channels. In some embodiments, kits disclosed herein may comprise agents that can specifically bind to TRPV4, ATP1A1, or both. In some embodiments, kits disclosed herein may comprise agents that can specifically bind to at least one invariant control plasma membrane marker binds to the transferrin receptor. In some embodiments, kits disclosed herein may further comprise antibodies that bind to one or more ion channels.

In some embodiments, kits disclosed herein may further comprise one or more distinct secondary antibodies that bind to one of the antibodies that specifically bind to plasma membrane localized ion channel proteins and other secondary antibodies that bind to one of the plasma membrane localized proteins of the at least one invariant control plasma membrane markers. In some aspects, secondary antibodies can be labeled with a detectable marker. In some embodiments, kits disclosed herein may further comprise antibodies that bind to a cytoplasmic protein control marker or a nuclear protein or DNA control marker, or a plasma membrane protein control marker.

In some embodiments, kits disclosed herein may comprise: 1) a plurality of agents, wherein the agents can specifically bind to at least two different types of ion channels, and 2) instructions for use of said plurality of agents and an agent for determining an increase in the plasma membrane localization of one or more ion channels. In some aspects, kits disclosed herein may comprise instructions for use of plurality of agents and an agent for determining an increase in the plasma membrane localization of said at least two ion channels by comparing the plasma membrane localization of said at least two ion channels to said at least one invariant control plasma membrane marker wherein an increase in the level of plasma membrane localization of said at least two ion channels as compared to the at least one invariant control plasma membrane marker is indicative of a DCIS at high risk of becoming invasive.

In some embodiments, kits disclosed herein may further comprise instructions for calculating an invasiveness risk score from said increase in the plasma membrane localization levels of one or more ion channels and comparing said invasiveness risk score to a control score. In some embodiments, kits disclosed herein may further comprise instructions for determining an increase in the plasma membrane localization levels of one or more ion channels by using a multivariate prediction model to determine if a pattern of localization of said one or more ion channels is indicative of a DCIS of high likelihood of becoming invasive.

In some embodiments, kits disclosed herein may be used wherein the breast abnormality and/or pathology has previously been identified as ductal carcinoma in situ. In some embodiments, kits disclosed herein may be used wherein the breast abnormality and/or pathology has previously been identified as ductal carcinoma in situ based on calcification detected by mammography.

In certain embodiments, the present disclosure provides methods of preparing a sample for assessment of treating a subject having or suspected of having at least one a breast abnormality. In some embodiments, the present disclosure provides methods of preparing a sample for assessment of treating a subject having or suspected of having an invasive breast cancer. In certain embodiments, the present disclosure provides methods of preparing a sample for assessment of treating a subject having or suspected of having high-grade DCIS. In certain embodiments, the present disclosure provides methods of characterizing a DCIS in a subject having or suspected of having high-grade DCIS. In some aspects, methods of characterizing a high-grade DCIS may comprise: (i) collecting a tissue sample from the breast of the subject, wherein the breast tissue sample has or is suspected of having at least one DCIS cell; (ii) preparing the tissue sample for histological analysis; (iii) contacting the prepared tissue sample with reagents that bind one or more ion channels selected from the group consisting of TRPV4 and ATP1A1; (iv) quantitating the number of cancer cells having one or more ion channels localized to the plasma membrane of the DCIS cell; and (v) characterizing the breast abnormality in the subject as high grade ductal carcinoma in situ (DCIS) and/or invasive ductal carcinoma (IDC) when one or more of the DCIS cells have one or more ion channels localized to the plasma membrane of the cancer cell. In some embodiments, methods disclosed herein may further comprise administering chemotherapy, administering radiation, administering a targeted therapy, surgically removing breast tissue, or any combination thereof when one or more of the cancer cells has one or more ion channels localized to the plasma membrane of the cancer cell.

The foregoing is intended to be illustrative and is not meant in a limiting sense. Many features and subcombinations of the present inventive concept may be made and will be readily evident upon a study of the following specification and accompanying drawings comprising a part thereof. These features and subcombinations may be employed without reference to other features and subcombinations.

BRIEF DESCRIPTION OF THE FIGURES

The patent or application file contains at least one drawing executed in color. Copies of this patent or patent application with color drawing(s) will be provided by the Office by request and payment of the necessary fee.

The following drawings form part of the present specification and are included to further demonstrate certain embodiments of the present disclosure. Certain embodiments can be better understood by reference to one or more of these drawings in combination with the detailed description of specific embodiments presented herein.

FIG. 1A shows normal breast duct progression to atypical ductal hyperplasia (ADH) to ductal carcinoma in situ (DCIS) and to invasive ductal carcinoma (IDC).

FIG. 1B shows a model of how cell crowding alters biomechanical features, reducing cell volume and increasing cortical cell stiffness wherein these changes then selectively alter the trafficking pattern of ion channels to translocate to the plasma membrane (PM), which primes cells for invasion.

FIG. 2A shows that cell (DCIS.com) crowding (N to OC) reduced (downward arrow) cell volume (V) and increased (upward arrow) stiffness (Young's modulus; Y). Unpaired and non-parametric t-test. ****: <0.0001. FIG. 2B shows that cell crowding selectively increased invasive potential of DCIS-.com and CA1a (a positive control) cells. Cell number effects were normalized to assess invasiveness. Scale bar=100 µm.

FIGS. 3A-3D depict schematics and graphs illustrating variability in cell volume and stiffness of a cell as an indicator of invasion capacity. FIG. 3A shows a schematic of cell crowding induced volume reduction. FIGS. 3B-3D show graphs demonstrating direct measurements of volume (FIGS. 3B and 3D) and stiffness (FIG. 3C) in cells before and after crowding.

FIG. 4A shows that cell crowding enriched TRPV4 in the PM only in DCIS.com but not in AT1 (ADH analogue) and 10A (normal). Transferrin receptor (TfR) distribution was insensitive to cell crowding. IF images. FIG. 4B shows IF images of OC DCIS.com cells treated with 20 nM lithium bicarbonate (ATP1a1 inhibitor) and 100 nM ouabain (ATP1a1 agonist) for 24 hours, where ouabain, not lithium bicarbonate perturbed PM ATP1a1 localization. Scale bar=10 µm.

FIG. 5A shows a schematic of the method where D: day, N: Normal density (40-70%), D-2: Two days before confluence (D0); Con: Confluence (100%), OC: Overconfluence, usually reached at D5 and onward. FIG. 5B shows bright-field images of cells captured on marked days. Scale bar=100 µm. FIG. 5C shows that cell crowding induced cell volume and stiffness changes were assessed by a confocal microscope that captures 3D volume of single RFP expressing cells (right image) and a nanoindenter device that can indent a single cell to readout the response (load vs indentation curve) to extract out the Young's modulus in the elastic regime (dashed box) using a Hertzian model. The indentation probe used had a spring constant (0.24 N/m) and tip diameter (10 µm). RFP expression did not noticeably alter cell volume (range is within 10%).

FIGS. 6A-6G depict images illustrating 2D hydrogel-based invasion assays. FIG. 6A shows a schematic of how to perform an exemplary 2D hydrogel-based invasion assay. FIGS. 6B-6E show images of from a representative assay where: FIG. 6B (invasion gel) shows fluorescent dye labeled gelatin degraded (black areas) as a result of cell invasion; FIG. 6C (DAPI) shows cell nuclei labeling; FIG. 6D (invasion area) shows a binary image that indicated invasion area (magenta); and FIG. 6E (invading cells) shows detected spots that fell into the masked areas that informed the cell subset that have invaded. Percent (%) invading cells was calculating by dividing this value by the total number of spots. FIGS. 6F-6G show images demonstrating that the ATP1A1 distribution in DCIS.com cells grown in 0.43 kPa substrates (FIG. 6F) vs 2 kPa substrates (FIG. 6G) did not vary between two stiffness conditions. Scale bar=100 µm (FIGS. 6B-6E) and 10 µm (FIGS. 6F-6G).

FIGS. 7A-7D depict images and graphs illustrating localization of ion channels in the cell plasma membrane. FIG. 7A shows mass spectrometry data demonstrating the proteins that were enriched in the PM>5 fold when cells were confluent. Ion channels (including TRPV4) and a growth factor receptor (IGF1R) are indicated by orange and purple boxes, respectively. FIG. 7B shows images of PM proteins that were pulled down after cell-surface biotinylation with streptavidine (SA) beads and immunoblotted for TRPV4 and ATP1A1. DCIS.com and CA1a show increased PM protein levels when OC densities were reached. FIG. 7C shows images of overall proteins levels of ion channels that were similar across four 10A cell derivatives. FIG. 7D shows 3D SIM images of TRPV4 (magenta) with GM130 (green; golgi) showing overlay (white).

FIG. 8A shows immunohistochemistry (IHC) images demonstrating TRPV4 staining of normal breast (negative), ADH (nuclear), and high-grade DCIS (PM) regions. The comedo DCIS region showed various PM focal staining of TRPV4 (PM; indicated by black arrows). Scale bars=200 mm (Top), 40 and 60 mm (middle) and 10 mm (bottom). FIG. 8B shows TRPV4 staining in cell line examples where ADH cells show nuclear (N; indicated by black arrow) staining. ND: normal density. OC: overconfluent. Scale bar=10 mm.

FIGS. 10A-10D depict images and graphs illustrating enrichment of ion channels at the plasma membrane of DCIS cells treated with 0% PEG (FIG. 10A), 2% PEG (FIG. 10B), 5% PEG (FIG. 10C), and 10% PEG (FIG. 10D) for 24 hours.

FIGS. 11A-11D depict images and graphs illustrating independent possibilities for crowding-mediated increased invasiveness. FIG. 11A shows a graph demonstrating YAP mRNA amounts in DCIS cells that were overconfluent (OC) versus normal (N) density. FIG. 11B shows a graph demonstrating cell cycle arrest in DCIS cells treated with vehicle (control) or the cell cycle inhibitor, Trichostatin A (TSA). FIGS. 11C-11D show images of DCIS.com cell invasiveness after treatment with vehicle or TSA (FIG. 11C) and the percentage of invasive cells per treatment group (FIG. 11D).

DEFINITIONS

Figure 1A:
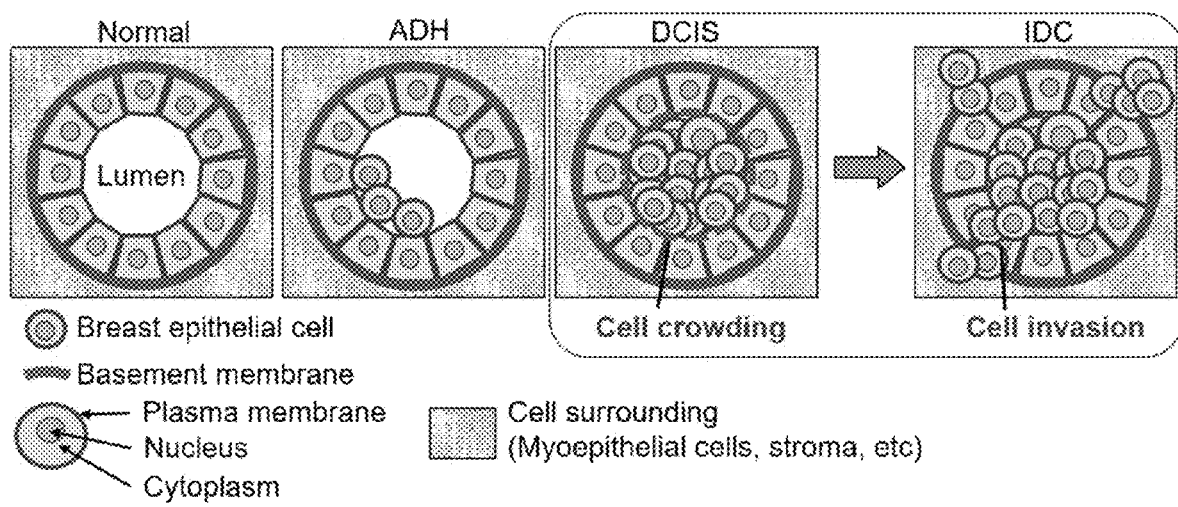
FIGS. 1A-1B depict schematics illustrating disease progression of ductal breast cancer and cell crowding in DCIS cells.

Terms, unless defined herein, have meanings as commonly understood by a person of ordinary skill in the art relevant to certain embodiments disclosed herein or as applicable.

As used herein "about" unless otherwise indicated, applies to all numbers expressing quantities of agents and/or compounds, properties such as molecular weights, reaction conditions, and as disclosed herein are contemplated as being modified in all instances by this term. Accordingly, unless indicated to the contrary, the numerical parameters in the specification and claims are approximations that can vary from about 10% to about 15% plus and/or minus depending upon the desired properties sought as disclosed herein. Numerical values as represented herein inherently contain standard deviations that necessarily result from the errors found in the numerical value's testing measurements.

As used herein, "individual", "subject", "host", and "patient" can be used interchangeably herein and refer to any mammalian subject for whom diagnosis, treatment, prophylaxis or therapy is desired, for example, humans, pets, livestock, horses or other animals. In some embodiments, a subject may be a rodent, e.g., a mouse, a rat, a guinea pig, etc. In other embodiments, a subject may be a livestock animal. Non-limiting examples of suitable livestock animals may include pigs, cows, horses, goats, sheep, llamas and alpacas. In yet other embodiments, a subject may be a companion animal. Non-limiting examples of companion animals may include pets such as dogs, cats, rabbits, and birds. In yet other embodiments, a subject may be a zoological animal. As used herein, a "zoological animal" refers to an animal that may be found in a zoo. Such animals may include non-human primates, large cats, wolves, and bears. In other embodiments, the animal is a laboratory animal. Non-limiting examples of a laboratory animal may include rodents, canines, felines, and non-human primates. In some embodiments, the animal is a rodent. Non-limiting examples of rodents may include mice, rats, guinea pigs, etc. In preferred embodiments, the subject is a human.

As used herein, the terms "therapeutically effective amount" or "therapeutically effective dose," or similar terms used herein are intended to mean an amount of an agent (e.g., chemotherapy, targeted treatments) and/or a therapy (e.g., radiation, surgery) that will elicit the desired biological or medical response (e.g., an improvement in one or more symptoms of a cancer).

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment. Accordingly, "treat," "treating," or "treatment" can refer to reversing, ameliorating, or inhibiting onset or inhibiting progression of a health condition or disease or a symptom of the health condition or disease (e.g., cancer).

As used herein, "marker" can refer to any molecule that can be measured or detected, for example. For example, a marker can include, without limitations, a nucleic acid, such as, a transcript of a gene, a polypeptide product of a gene, a glycoprotein, a carbohydrate, a glycolipid, a lipid, a lipoprotein, a carbohydrate, and/or a small molecule. As used herein, "expression" and grammatical equivalents thereof, in the context of a marker, can refer to the production of the marker as well as the level or amount of the marker, or the cellular localization and/or accumulation of the marker within a cell.

DETAILED DESCRIPTION

In the following sections, certain exemplary compositions and methods are described in order to detail certain embodiments of the invention. It will be obvious to one skilled in the art that practicing the certain embodiments does not require the employment of all or even some of the specific details outlined herein, but rather that concentrations, times and other specific details can be modified through routine experimentation. In some cases, well known methods, or components have not been included in the description.

The present disclosure is based, at least in part, on the novel discovery of single-cell level determinants of the invasive transition of DCIS cells and that these determinants can be leveraged as diagnostic markers. Currently, there is no robust prognostic factor that can distinguish pro-invasive or high-risk DCIS cells from low-risk DCIS cells. Many studies have tried to address this issue by looking for genetic factors associated with high-risk DCIS tumors. However, despite significant efforts, no known markers or profiles have been found that consistently correlate with the likelihood of DCIS becoming an invasive disease. This is likely due to the high degree of genetic heterogeneity that exists in DCIS tumors. Without being bound by theory, this problem is overcome in the present disclosure by looking at phenotypic characteristics associated with high-risk DCIS cells, such as cell volume and stiffness and also the subcellular localization of specific proteins, to assess DCIS cells for their risk of becoming invasive.

Identifying mechanisms that promote DCIS transition to invasive disease as disclosed herein enables better classification of DCIS, particularly in terms of identifying high-risk cases. Assessment of the risk of DCIS becoming invasive, progressing to ductal carcinoma (IDC), is clinically important because low-risk DCIS is benign and may not need to be treated. A large percentage of all DCIS tumors (stage 0 breast cancer) remain benign and non-invasive, and these do not pose a threat to the patient. In contrast, IDC is dangerous and categorized as stage 1-4 breast cancer. It is therefore treated aggressively, typically with surgery and radiation. Unfortunately, because there are currently no methods for determining which DCIS tumors are at high risk of progressing to invasive disease, most DCIS patients also undergo aggressive treatment with surgery, radiation, and anti-hormone agents. In some cases, this surgery includes radical mastectomy in which the entire breast is removed. The ability to identify DCIS cases that are most likely to transition to IDC can enable clinicians to reserve surgical intervention for those who would most benefit from it. At the same time, it can allow low-risk DCIS patients to avoid unnecessarily aggressive treatment and the negative impact this would have on their quality of life.

I. Methods of Diagnosing Risk of DCIS

In general, methods disclosed herein may include detecting one or more markers of cancer in a subject from at least one sample collected from said subject. In some aspects, at least one sample can be obtained from a subject who has not been diagnosed with a cancer. In some other aspects, at least one sample can be obtained from a subject who has been diagnosed with a cancer. In some aspects, at least one sample can be obtained from a subject who presents with at least one symptom of a cancer. In some embodiments, methods herein may include detecting one or more markers of breast cancer in a subject from at least one sample collected from said subject. In some embodiments, at least one sample can be obtained from a subject who has not been diagnosed with breast cancer, is suspected of having breast cancer, or who has been diagnosed with breast cancer. In some other aspects, at least one sample can be obtained from a subject who has or is suspected of having one or more breast abnormalities.

Methods provided in certain embodiments disclosed herein may include detecting one or more markers of high-grade DCIS in a subject from at least one sample collected from said subject. In some aspects, at least one sample can be obtained from a subject who has not been diagnosed with DCIS. In some other aspects, at least one sample can be obtained from a subject who has been diagnosed with DCIS. In some aspects, at least one sample can be obtained from a subject who presents with at least one symptom of DCIS.

In some embodiments, a sample obtained from a subject to detect one or more markers of high-grade DCIS as disclosed herein may be a tissue sample, a blood sample, a plasma sample, a hair sample, venous tissues, cartilage, a sperm sample, a skin sample, an amniotic fluid sample, a buccal sample, saliva, urine, serum, sputum, bone marrow or a combination thereof. In some embodiments, a sample obtained from a subject to detect one or more markers of high-grade DCIS as disclosed herein may be a breast tissue sample. Non-limiting methods suitable for use herein to collect tissue samples can include collection by fine needle aspirate, by removal of pleural or peritoneal fluid, by excisional biopsy, and the like. In some aspects, a tissue sample can include a biopsy from a breast tissue abnormality, a biopsy from at least one tissue in contact with the breast tissue abnormality, and any combination thereof. In some aspects, a biopsy sample of the breast tissue abnormality and/or at least one tissue in contact with the breast tissue abnormality can be from about 10 mg about 50 mg (e.g., about 10 mg, 15 mg, 20 mg, 25 mg, 30 mg, 35 mg, 40 mg, 45 mg, 50 mg) of tissue per sample.

Carcinoma of the breast can arise from either the lobular or the ductal epithelium. Before breast cancer reaches the invasive stage at which point it can spread to the rest of the body, it is referred to as a pre-invasive lesion. In pre-invasive lesions, the abnormal cells are confined to the ducts or lobules from which they originate and have not yet broken the basement membrane. This progresses to ductal carcinoma in situ (DCIS), which is identified as a complete filling of the mammary duct with abnormal cells or atypical ductal hyperplasia (ADH). Once the myoepithelium is breached and tumor cells escape beyond the mammary duct confinement, the cancer is classified as an invasive ductal carcinoma (IDC).

In certain embodiments, methods herein may include detecting one or more markers of high-grade DCIS in a subject having or suspected of having at least one breast tissue abnormality. In some embodiments, methods herein may include detecting one or more markers of high-grade DCIS in a subject having or suspected of having a pre-invasive lesion. In some aspects, methods herein may include detecting one or more markers of high-grade DCIS in at least one tissue sample harvested from a pre-invasive lesion collected from said subject. In certain embodiments, methods herein may include detecting one or more markers of high-grade DCIS in a subject having or suspected of having a DCIS lesion. In some aspects, methods herein may include detecting one or more markers of high-grade DCIS in at least one tissue sample harvested from a DCIS lesion collected from said subject.

In certain embodiments, methods disclosed herein may be used to determine the likelihood of a DCIS becoming invasive. In some embodiments, methods herein may include detecting one or more markers of high-grade DCIS in a subject having or suspected of having a DCIS lesion to determine the likelihood of the DCIS lesion becoming invasive. In some aspects, methods herein can characterize a DCIS lesion as having a low risk of becoming invasive. In some aspects, methods herein can characterize a DCIS lesion as having a high risk of becoming invasive. In certain embodiments, methods disclosed herein may be used treat breast cancer by assessing the likelihood of a DCIS lesion becoming invasive.

a. Markers of DCIS Invasiveness

The present disclosure is based on, in part, the discovery that resting cell volume/stiffness, variability of cell volume between resting and crowded states, and/or translocation of proteins to the cancer cell plasma membrane correlate with cancer invasiveness. In some embodiments, one or more markers of high-grade DCIS as disclosed herein may include at least one protein localized at the plasma membrane of a cancer cell. As used herein, "localized" refers to a change in protein abundance in one part of the cell compared to a protein abundance in a different part of the cell. In some examples, a protein localized to a plasma membrane of a DCIS cell has a higher abundance at the plasma membrane compared to the other cellular locations. In certain embodiments, one or more markers of high-grade DCIS as disclosed herein may include at least one ion channel localized at the plasma membrane of a DCIS cell.

In certain embodiments, the presence of one or more ion channels localized at the plasma membrane of a DCIS cell of a subject herein may be indicative of the subject having high-grade DCIS. In some embodiments, the presence of one or more ion channels localized at the plasma membrane of a DCIS cell of a subject herein may be indicative of the subject having a pro-invasive or high-risk lesion. In some embodiments, the presence of one or more ion channels localized at the plasma membrane of a cancer cell of a subject herein may be indicative of the subject having a DCIS lesion. In some embodiments, the presence of one or more ion channels localized at the plasma membrane of a DCIS cell of a subject herein may be indicative of the subject having a DCIS lesion at high risk of becoming invasive. In some embodiments, the presence of one or more ion channels localized at the plasma membrane of a DCIS cell of a subject herein may be indicative of the subject having a DCIS lesion at high risk of progressing into IDC. In some embodiments, the presence of one or more ion channels localized at the plasma membrane of a DCIS cell of a subject herein may be a precursor to breast cancer.

In some embodiments, one or more markers of high-grade DCIS as disclosed herein may include at least one ion channel localized at the plasma membrane of a DCIS cell wherein the least one ion channel may be KCNN4 (Potassium Calcium-Activated Channel Subfamily N Member 4), SCN11A (Sodium Voltage-Gated Channel Alpha Subunit 11), TRPV4 (transient receptor potential vanilloid-type 4), ATP1A1 (ATPase Na+/K+Transporting Subunit Alpha 1), or any combination thereof. In some aspects, one or more markers of high-grade DCIS as disclosed herein may include TRPV4, ATP1A1, or both localized at the plasma membrane of a DCIS cell.

In certain embodiments, the presence of TRPV4, ATP1A1, or both localized at the plasma membrane of a DCIS cell of a subject herein may be indicative of the subject having a high-grade DCIS. In some embodiments, the presence of TRPV4, ATP1A1, or both localized at the plasma membrane of a DCIS cell of a subject herein may be indicative of the subject having a pro-invasive lesion. In some embodiments, the presence of TRPV4, ATP1A1, or both localized at the plasma membrane of a DCIS cell of a subject herein may be indicative of the subject having a high-grade DCIS lesion. In some embodiments, the presence of TRPV4, ATP1A1, or both localized at the plasma membrane of a DCIS cell of a subject herein may be indicative of the subject having a high-grade DCIS lesion at high risk of becoming invasive. In some embodiments, the presence of TRPV4, ATP1A1, or both localized at the plasma membrane of a DCIS cell of a subject herein may be indicative of the subject having a DCIS lesion at high risk of progressing into IDC.

In certain embodiments, a multivariate prediction model may be used to determine if a pattern of plasma membrane localization of said one or more ion channels is indicative of a DCIS with high risk of becoming invasive. A multivariate prediction model may use one or more prognostic factors associated with subsequent invasive breast cancer in combination with the pattern of plasma membrane localization of the one or more ion channels determined according to the methods disclosed herein. Non-limited examples of prognostic factors for subsequent invasive breast cancer that may be used in the multivariate prediction models disclosed herein include high histologic grade, young age at DCIS diagnosis, solid DCIS architecture, detection by palpation, premenopausal status, race, presence of calcification, high p16 expression, high COX-2 expression, presence of periductal fibrosis, and any combination thereof.

b. Methods of Detection

Methods embodied herein can include the detection and/or quantitation of ion channels (e.g., TRPV4, ATP1A1, or both) localized at the plasma membrane of a DCIS cell of a subject herein for diagnosis of a high-grade DCIS. In some embodiments, a tissue sample collected from a subject having or suspected of having high-grade DCIS may be analyzed by histochemistry, including but not limited to immunohistochemistry, in situ hybridization, flow cytometry, immunocytochemistry and the like, for the presence of cells that have one or more ion channels localized at the plasma membrane. For analysis by histology methods herein, sections, which may be frozen, embedded in paraffin, etc. are taken from a sample as disclosed herein. Once a sample is obtained, it can be used directly, frozen, or maintained in appropriate culture medium for short periods of time. The samples may be obtained by any convenient procedure. In some embodiments, where analysis by flow cytometry is desired, the tissue sample can be dissociated, and the cell suspension may be separated by centrifugation, elutriation, density gradient separation, apheresis, affinity selection, panning, FACS, centrifugation with Hypaque, etc. prior to analysis.

In certain embodiments, the presence of said one or more ion channels localized at the plasma membrane may be detected using antibodies or antibody fragments that bind to one or more ion channels. In some embodiments, antibodies or antibody fragments that bind to one or more ion channels can be directly labeled with a label. In some aspects, a label may be a fluorescent marker or with an enzyme, a small molecule such as biotin that is the target of a binding protein, contrast agent such as nanoparticles, or any combination thereof. In some embodiments, the presence of said one or more ion channels localized at the plasma membrane may be detected using antibodies or antibody fragments that bind to one or more ion channels wherein a second antibody can bind to the antibodies or antibody fragments that bind to said one or more ion channels, wherein said second antibody is labeled with a label disclosed herein. In some aspects, antibodies or antibody fragments that bind to one or more ion channels and, optionally, their corresponding a second antibody, may be used in any of the methods as disclosed herein for determining the presence of said one or more ion channels localized at the plasma membrane.

In some embodiments, antibodies or antibody fragments that bind to one or more ion channels may be used in any of the methods disclosed herein to detect the presence of KCNN4, SCN11A, TRPV4, ATP1A1 or any combination thereof in a plasma membrane of a cell. In some aspects, antibodies or antibody fragments that bind to one or more ion channels may be used in any of the methods disclosed herein to detect the presence of TRPV4 or ATP1A1 in a plasma membrane in a cell. In some other aspects, antibodies or antibody fragments that bind to one or more ion channels may be used in any of the methods disclosed herein to detect the presence of TRPV4 and ATP1A1 in a plasma membrane in a cell. Where simultaneous detection of TRPV4 and ATP1A1 in a plasma membrane is performed, a second antibody that binds to a TRPV4 primary antibody can have a label that differs from that attached to a second antibody that binds to a ATP1A1 primary antibody. In other aspects where simultaneous detection of TRPV4 and ATP1A1 in a plasma membrane is performed, an antibody or antibody fragments that binds to TRPV4 can be directly attached to a label that differs from the label directly attached to an antibody or antibody fragments that binds to ATP1A1.

In some embodiments, localization of ion channels (e.g., TRPV4, ATP1A1, or both) at the plasma membrane of a breast tissue cell herein may be detected and/or quantitated by subjecting a tissue sample from a subject disclosed herein to immunohistochemical (IHC) analysis. In immunohistochemical analysis, the tissue is first processed either as paraffin-embedded block or as a frozen tissue and is further sliced at certain thickness before the tissue slice is placed on a slide. Next, the slide is going through a typical immunodetection process to form immunocomplex between antigen of interest and detection antibody on the slide. In some aspects, the antigen of interest herein is for an ion channel. In some other aspects, the antigen of interest herein is for KCNN4, SCN11A, TRPV4, ATP1A1, or any combination thereof. In still some other aspects, the antigen of interest herein is for TRPV4, ATP1A1, or any combination thereof. A pre-labeled antibody can be used to allow the detection of antigen of interest on the slide by a pathologist with the aid of microscope. For slice from paraffin-embedded block, the slice can go through further steps to facilitate antigen-antibody interaction. These steps may include, but are not limited to, de-paraffin of the slice, and antigen retrieval step to expose the antigen for antigen-antibody interaction.

II. Methods of Treatment

In general, methods disclosed herein include treating a subject having or suspected of having a high-grade DCIS by detecting localization of one or more markers of high-grade DCIS in the plasma membrane of a cell from at least one sample collected from said subject. In certain embodiments, the present disclosure provides methods of collecting a tissue sample from a subject having or suspected of having breast abnormality, detecting the localization of one or more markers of high-grade DCIS (e.g., ion channels) in the plasma membrane of a cell in the tissue sample, and administering the appropriate treatment based on the localization of the of one or more markers of high-grade DCIS (e.g., ion channels) in the plasma membrane.

Embodiments herein also include methods of detecting a breast abnormality that is a precursor to breast cancer wherein localization of one or more markers of high-grade DCIS in the plasma membrane of a cell from at least one sample collected from a subject having the breast abnormality is indicative of a likelihood of the breast abnormality becoming a breast cancer. In some aspects, methods herein may include detecting a breast cancer in a subject identified as having at least one breast abnormality that is a precursor to breast cancer.

In certain embodiments, the appropriate treatment of a subject may depend on the detection of the localization of one or more ion channels in the plasma membrane of a cell in the tissue sample. In some embodiments, the appropriate treatment of a subject may depend on the detection of the localization of TRPV4, ATP1A1, KCNN4, SCN11A, or any combination thereof in the plasma membrane of a cell in the tissue sample. In some embodiments, the appropriate treatment of a subject may depend on the detection of the localization of TRPV4, ATP1A1, or any combination thereof in the plasma membrane of a cell in the tissue sample.

In general, the reduced risk of metastatic breast cancer associated with localization of ion channels at the plasma membrane may be used to favor less invasive and less extensive treatment options, and thus reduce over-treatment of patients with potentially toxic, mutilating or costly procedures and regimes.

In certain embodiments, a subject herein not having localization of one or more ion channels (e.g., TRPV4, ATP1A1) detected in the plasma membrane of a cell in the tissue sample collected from the subject may have a DCIS with a low likelihood of becoming invasive. In some embodiments, the appropriate treatment of a subject not having localization of one or more ion channels (e.g., TRPV4, ATP1A1) detected in the plasma membrane of a cell in the tissue sample may be monitoring the subject without administering a breast cancer treatment regimen.

In certain embodiments, a subject herein having localization of one or more ion channels (e.g., TRPV4, ATP1A1) detected in the plasma membrane of a cell in the tissue sample collected from the subject may have a DCIS with a high likelihood of becoming invasive. In some embodiments, the appropriate treatment of a subject having localization of one or more ion channels (e.g., TRPV4, ATP1A1) detected in the plasma membrane of a cell in the tissue sample according to the methods herein may prevent breast cancer progression. In some embodiments, the appropriate treatment of a subject having localization of one or more ion channels (e.g., TRPV4, ATP1A1) detected in the plasma membrane of a cell in the tissue sample according to the methods herein may ameliorate one or more symptoms associated with invasive progression of DCIS. In some embodiments, the appropriate treatment of a subject having localization of one or more ion channels (e.g., TRPV4, ATP1A1) detected in the plasma membrane of a cell in the tissue sample according to the methods herein may reduce risk of breast cancer recurrence in the subject. In some embodiments, the appropriate treatment of a subject having localization of one or more ion channels (e.g., TRPV4, ATP1A1) detected in the plasma membrane of a cell in the tissue sample according to the methods herein may slow tumor growth in the subject. In some embodiments, the appropriate treatment of a subject having localization of one or more ion channels (e.g., TRPV4, ATP1A1) detected in the plasma membrane of a cell in the tissue sample according to the methods herein may reduce the risk of metastasis in the subject.

In certain embodiments, a subject herein having localization of one or more ion channels (e.g., TRPV4, ATP1A1) detected in the plasma membrane of a cell in the tissue sample collected from the subject may be administered one or more anticancer therapies. Anticancer therapy as used herein refers to a treatment regimen for the treatment of malignant, or cancerous disease (e.g., breast cancer). Non-limiting examples of anticancer therapies can include administration of an anticancer drug, radiation, surgical methods, chemotherapy, targeted therapy, and the like.

Determining the risk of invasive DCIS associated with localization of ion channels in the plasma membrane using the methods herein may result in the treatment of high-grade DCIS and/or breast cancer to be administered involving a less invasive breast conserving surgery, or lumpectomy, over a mastectomy. In some embodiments, tissue samples having little to no localization of ion channels (e.g., TRPV4, ATP1A1) in the plasma membrane using the methods herein may result in no surgical administration for treating high-grade DCIS and/or breast cancer. In some embodiments, tissue samples having little to no localization of ion channels (e.g., TRPV4, ATP1A1) in the plasma membrane using the methods herein may result in a lumpectomy for treating high-grade DCIS and/or breast cancer. In some embodiments, tissue samples having some to high localization of ion channels (e.g., TRPV4, ATP1A1) in the plasma membrane using the methods herein may result in a mastectomy for treating high-grade DCIS and/or breast cancer. In some embodiments, tissue samples collected from a subject after having one or more surgical treatments for breast cancer having some to high localization of ion channels (e.g., TRPV4, ATP1A1) in the plasma membrane may be administered supplemental radiation and/or chemotherapy. In some embodiments, tissue samples collected from a subject after having one or more surgical treatments for breast cancer having little to no localization of ion channels (e.g., TRPV4, ATP1A1) in the plasma membrane may not need supplemental radiation and/or chemotherapy.

In some embodiments, tissue samples having little to no localization of ion channels (e.g., TRPV4, ATP1A1) in the plasma membrane using the methods herein may result in no administration of radiation therapy for treating high-grade DCIS and/or breast cancer. In some embodiments, tissue samples having some to high localization of ion channels (e.g., TRPV4, ATP1A1) in the plasma membrane using the methods herein may result in administration of radiation therapy for treating high-grade DCIS and/or breast cancer. Non-limiting examples of radiation therapy for treating high-grade DCIS and/or breast cancer include external beam radiation therapy, whole breast radiation, hypofractionated radiation therapy, accelerated partial breast irradiation, chest wall radiation, lymph node radiation, and any combination thereof.

In some embodiments, tissue samples having little to no localization of ion channels (e.g., TRPV4, ATP1A1) in the plasma membrane using the methods herein may result in no administration of chemotherapy drugs for treating high-grade DCIS and/or breast cancer. In some embodiments, tissue samples having some to high localization of ion channels (e.g., TRPV4, ATP1A1) in the plasma membrane using the methods herein may result in administration of one or more chemotherapy drugs for treating high-grade DCIS and/or breast cancer. In some aspects, tissue samples having some to high localization of ion channels (e.g., TRPV4, ATP1A1) in the plasma membrane using the methods herein may result in administration of neoadjuvant chemotherapy. In some other aspects, tissue samples having some to high localization of ion channels (e.g., TRPV4, ATP1A1) in the plasma membrane using the methods herein may result in administration of adjuvant chemotherapy. Non-limiting more chemotherapy drugs suitable for use herein include anthracyclines, such as doxorubicin (Adriamycin), epirubicin (Ellence), and liposomal doxorubicin (Doxil); taxanes, such as paclitaxel (Taxol), docetaxel (Taxotere), Paclitaxel (Taxol), docetaxel (Taxotere), and albumin-bound paclitaxel (Abraxane); 5-fluorouracil (5-FU); capecitabine (Xeloda); cyclophosphamide (Cytoxan); platinum agents, such as cisplatin and carboplatin (Paraplatin); ixabepilone (Ixempra); eribulin (Halaven); vinorelbine (Navelbine); gemcitabine (Gemzar); antibody drug conjugates, such as ado-trastuzumab emtansine (Kadcyla), fam-trastuzumab deruxtecan (Enhertu), sacituzumab govitecan (Trodelvy), and the like.

Estrogen, a female sex hormone produced by the ovaries, promotes growth of some breast cancers. In some embodiments, tissue samples having localization of ion channels (e.g., TRPV4, ATP1A1) in the plasma membrane using the methods herein may result in administration of one or more hormone therapies for treating high-grade DCIS and/or breast cancer. Non-limiting examples of hormone therapies suitable for use herein include goserelin (Zoladex), leuprolide (Lupron), anastrozole (Arimidex), letrozole (Femara), tamoxifen (Nolvadex), toremifene (Fareston), fulvestrant (Faslodex), and the like.

Targeted therapy is directed at (target) proteins on breast cancer cells that help them grow, spread, and live longer. In some embodiments, tissue samples having little to no localization of ion channels (e.g., TRPV4, ATP1A1) in the plasma membrane using the methods herein may result in no administration of a targeted therapy for treating high-grade DCIS and/or breast cancer. In some embodiments, tissue samples having some to high localization of ion channels (e.g., TRPV4, ATP1A1) in the plasma membrane using the methods herein may result in administration of one or more targeted therapies for treating high-grade DCIS and/or breast cancer. Non-limiting examples of targeted therapies suitable for use herein include trastuzumab (Herceptin); pertuzumab (Perjeta); trastuzumab, pertuzumab, and hyaluronidase injection (Phesgo); margetuximab (Margenza); ado-trastuzumab emtansine (Kadcyla); fam-trastuzumab deruxtecan (Enhertu); lapatinib (Tykerb); neratinib (Nerlynx); tucatinib (Tukysa); palbociclib (Ibrance); ribociclib (Kisqali); abemaciclib (Verzenio); everolimus (Afinitor); alpelisib (Piqray); olaparib (Lynparza); talazoparib (Talzenna); sacituzumab govitecan (Trodelvy); and the like. In some aspects, a targeted therapy may be a CAR-T therapy.

In certain embodiments, breast cancer treatments and high-grade DCIS treatments administered according to the methods disclosed herein can improve patient life expectancy compared to the cancer life expectancy of an untreated subject with identical disease condition and predicted outcome. As used herein, "patient life expectancy" is defined as the time at which 50 percent of subjects are alive and 50 percent have passed away. In some embodiments, patient life expectancy can be indefinite following treatment according to the methods disclosed herein. In other aspects, patient life expectancy can be increased at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In some embodiments, patient life expectancy can be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In some embodiments, patient life expectancy can be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

III. Kits

The present disclosure provides kits for performing any of the methods disclosed herein. In some aspects, the present disclosure provides a kit for determining localization of one or more markers of high-grade DCIS or invasive cancer (e.g., ion channels) as disclosed herein, for diagnosing high and low risk DCIS, and treating DCIS. Such a kit may comprise a means for determining any of the combinations of breast cancer markers as disclosed herein. In some other aspects, the present disclosure provides a kit for determining localization of one or more markers of high-grade DCIS or invasive cancer (e.g., ion channels) as disclosed herein, for diagnosing a precursor to breast cancer, and treating a breast cancer.

In certain embodiments, kits disclosed herein may be used for carrying out the assays described above. In some embodiments, kits disclosed herein may contain at least one monoclonal antibody, fragments thereof, fusion proteins or chimeric antibody, or a non-antibody based binding probe specific for one of the markers disclosed herein and a conjugate comprising a specific binding partner for the marker antibody or binding probe and a label capable of producing a detectable signal. In some aspects, kits may have at least one monoclonal antibody, fragments thereof, fusion proteins or chimeric antibody for detecting TRPV4 and/or ATP1A1, or a non-antibody based binding probe specific for TRPV4 and/or ATP1A1, and a conjugate comprising a specific binding partner for the TRPV4 and/or ATP1A1 antibody or binding probe and a label capable of producing a detectable signal. The reagents can also include ancillary agents such as buffering agents, antigen retrieval solutions and reagents, and protein stabilizing agents (e.g., polysaccharides). The diagnostic kit can further comprise, where necessary, other components of the signal-producing system including agents for reducing background interference, control reagents or an apparatus or container for conducting the test.

Kits typically include a label indicating the intended use of the contents of the kit and instructions for use. The term label includes any writing, or recorded material supplied on or with the kit, or which otherwise accompanies the kit. Accordingly, this disclosure provides for kits for identifying a subject having a DCIS with a high likelihood of becoming invasive. Kits may further include guidance on suitable treatment regimens for subjects identified as having highly invasive DCIS or invasive cancer as determined by the kit.

EXAMPLES

The following examples are included to illustrate certain embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes can be made in some embodiments which are disclosed and still obtain a like or similar result without departing from the spirit and scope of the invention.

Introduction to Examples 1-8

Exemplary methods herein are toward addressing the overdiagnosis and overtreatment in ductal carcinoma in situ (DCIS). This pre-invasive form of breast cancer develops within the breast duct (FIG. 1A) and accounts for approximately 20% of newly diagnosed breast cancer cases each year in the United States. More than half of DCIS cases do not progress to invasive cancer. Nonetheless, patients with DCIS typically undergo aggressive surgical treatment causing tens of thousands of patients each year to experience unnecessary anxiety and significant physical discomfort. This aggressive approach reflects the lack of clinical tools to determine which patients might benefit from surgical procedures, which stems from a limited knowledge of DCIS pathogenesis. Identifying mechanisms that promote DCIS transition to invasive disease will enable better classification of DCIS, particularly in terms of identifying high-risk cases.

Figure 1B:
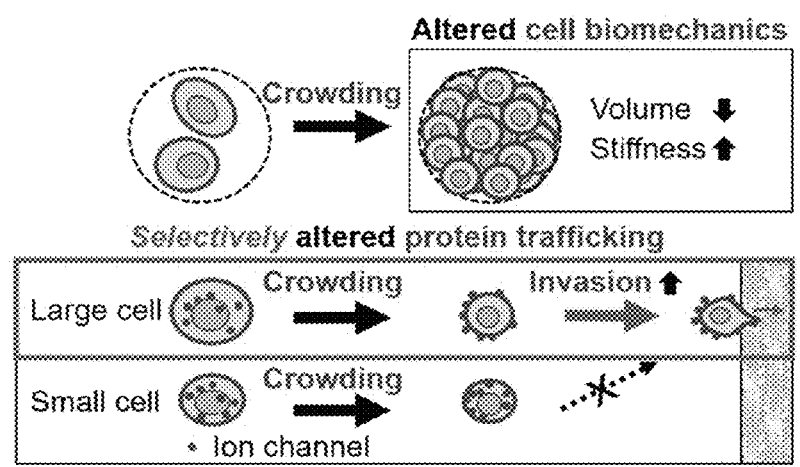

Exemplary methods herein were used to identify biomechanical alterations that promoted invasive transition of DCIS. Strategies employed in the present disclosure differ conceptually from the standard histopathologic and genetic approaches to investigate DCIS. Because all DCIS cells exist in a crowded microenvironment within the breast duct, exemplary methods herein were used to determine if this crowding affected the biomechanical properties of crowded cells and altered their biology toward an invasive phenotype. By identifying the biomechanical features and resultant biological behaviors that characterize pro-invasive DCIS cells, finding in the present disclosure accomplish major steps toward conquering overtreatment of DCIS (FIG. 1B).

Example 1

Exemplary methods herein demonstrated that there are single-cell level determinants of the invasive transition of DCIS cells and that can be leveraged as therapeutic targets and/or diagnostic markers. Methods herein utilized histologically 'high-grade DCIS' subtypes (cell lines and patient tissue samples) with comedo necrosis because of their high propensity for IDC transition and compared these subtypes to low-grade DCIS samples. Selected cell lines were those derived from MCF10A (basal, normal breast epithelial cells; "10A") including MCF10AT1 (pre-malignant cancer cells; "AT1"), MCF10DCIS.com (high-grade DCIS cells with comedo necrosis; "DCIS.com"), and MCF10CA1a (invasive cancer cells; "CA1a"). MCF7 (luminal type) and SKBR3 (HER2 positive) epithelial breast cancer cell lines were used as controls because these cells do not form DCIS in xenograft models. Results using these cell lies were compared to the corresponding patient samples that cover each stage of disease progression. Table 1 shows the cells and tissue specimens from patients used herein as categorized based on the tumor types marked with "X".

TABLE 1

|  | Nor | ADH | Low-DCIS | Inter-DCIS | High-DCIS | IDC |
|---|---|---|---|---|---|---|
| MCF10A | X |  |  |  |  |  |
| MCF10AT1 |  | X |  |  |  |  |
| MCFDCIS.com |  |  |  |  | X |  |
| MCFCA1a |  |  |  |  |  | X |
| Patient Sample | X | X | X | X | X | X |

In response to their microenvironment, cells adapt by undergoing biomechanical alterations, including cell stiffening and cell volume changes. Cancer cell invasion requires that cells squeeze through their surroundings, such as the extracellular matrix (ECM) or neighboring tissues, implying an alteration of cellular biomechanics. Highly motile cells are softer than less motile cells, suggesting that deformability may be a requirement for invasion. Direct measurement of cell volume during infiltration of the surrounding matrix shows that invading cells reduce their volumes. Using a protocol similar to Guo et al., PNAS (2017) Oct. 10; 114(41):E8618-E8627, the disclosure of which is incorporated herein in its entirety, cell volume and cell stiffness had a universal inverse relationship where reduced volume correlated with increased stiffness. Therefore, cell shrinkage during invasion indicated that cancer cells must stiffen to be invasive. As such, cell volume and stiffness are measurable properties that can be used to assess pro-invasiveness of a DCIS.

Figure 2A:
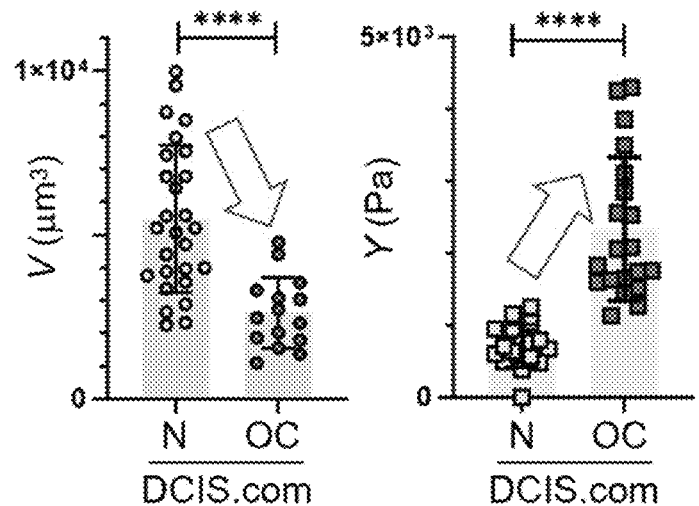
FIGS. 2A-2B depict schematics and graphs illustrating effects of cell crowding in ductal carcinoma in situ.
Figure 2B:
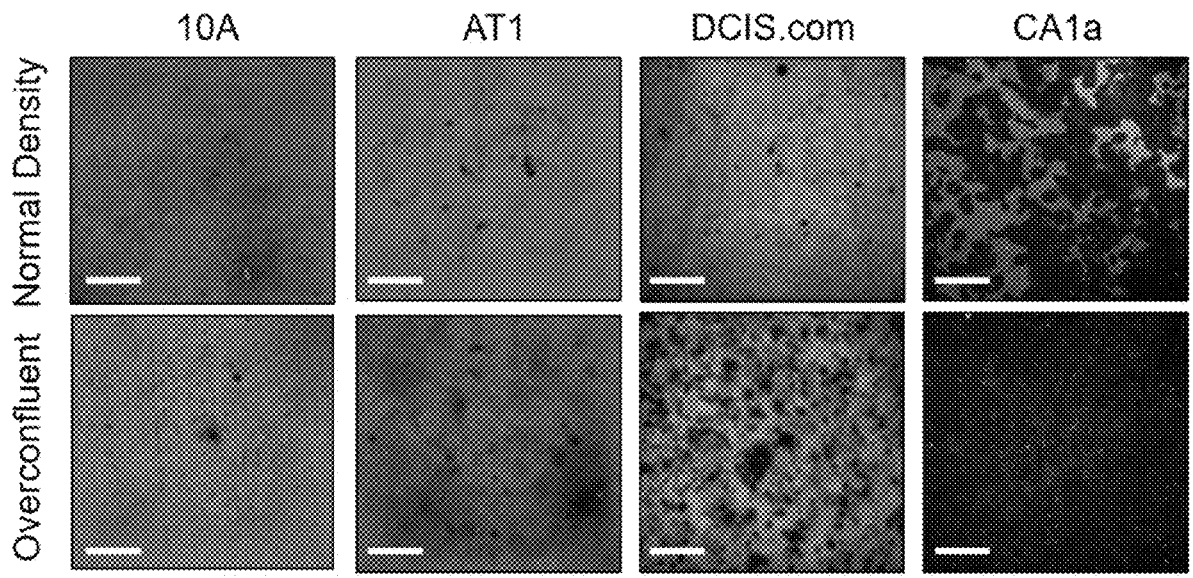

DCIS cells become crowded within the narrow intraductal space as they accumulate. FIG. 2A shows that, in vitro, cell crowding lowered cell volume and increased cortical stiffness. Crowding of a cell line (DCIS.com) that mimics high-grade DCIS with comedo necrosis, not benign cells, had increased invasiveness (FIG. 2B), as measured using a fully quantifiable, two-dimensional hydrogel-based invasion assay (FIG. 6A). These results suggested that the range of variability in cell volume or stiffness of a single cancer cell was an indicator of its invasion capacity (FIG. 3A). Accordingly, invasive cells that are softer than non-invasive cells can be interpreted as invasive cells undergoing greater cell volume changes than non-invasive cells. This is consistent with direct measurements of the differences in volume (FIG. 3B) and stiffness (FIG. 3C) of the same cell before and after crowding. The differences were higher for DCIS.com compared with more benign cells (10A and AT1) (FIG. 3A-3D).
I
Data showed that crowding-induced volume variability correlated with the cell volume ("$V_N$"), at a normal density and in a resting (not invading) state (FIGS. 3A and 3D). To statistically establish the positive relationship of volume variation ("$\Delta V$") and $V_N$ with invasiveness, in addition to the cell lines in Table 1, glioma cell lines (U-87MG, A-172, and U-251) which exhibit varying degrees of pro-invasiveness, as well as primary breast epithelial cells from patients with different disease states are also assessed.

Example 2

Exemplary methods herein demonstrated that biomechanical changes had functional consequences on cell biology in DCIS cells. Biomechanical adaptation to the local environment produces functional consequences that can alter cellular functions such as motility and signaling. Examples of the present disclosure identified how changes in biomechanics during crowding elicited cell biological changes that primed cells for invasion, specifically in high-grade DCIS cells compared with low-grade DCIS, ADH, and normal breast cells. Crowded DCIS.com cells showed changes in cell volume (FIG. 3B) or stiffness (FIG. 3C) that were greatest for high-grade DCIS cells (DCIS.com) than for normal and ADH cells. High-grade DCIS cells may therefore be primed to alter their biomechanical properties in response to external cues such as cell crowding, particularly compressing their volumes and increasing cortical stiffness to a greater degree than low-grade DCIS cells. As such, the data suggest that the larger magnitude of biomechanical responses induced by crowding in high-grade DCIS cells is a factor in their invasive progression.

Figure 4A:
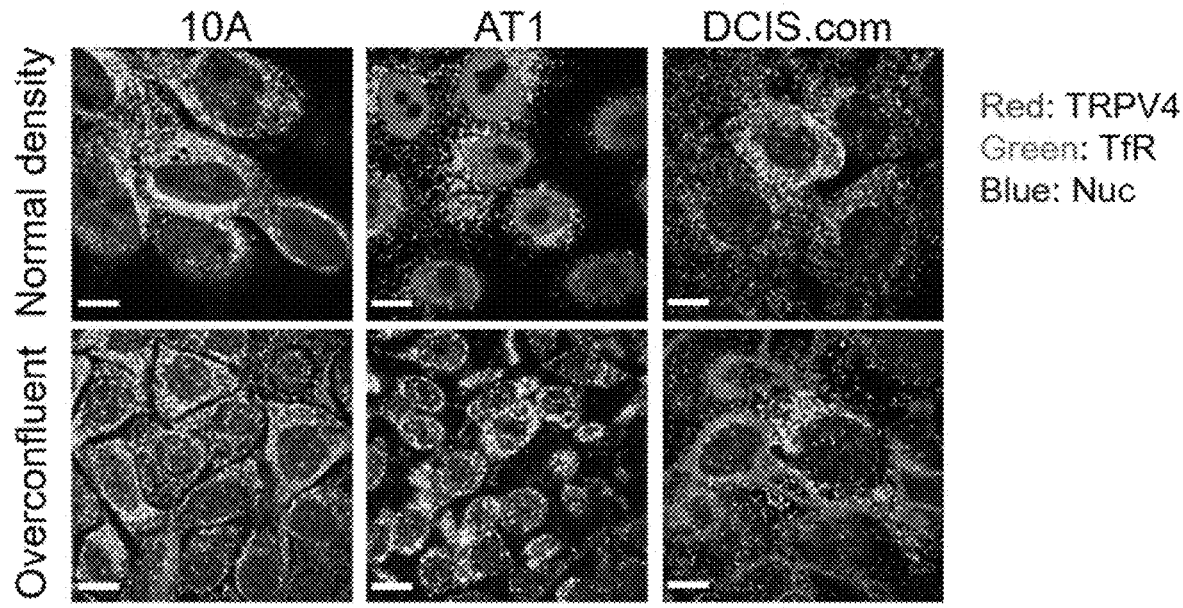
FIGS. 4A-4B depict images illustrating ion channel enrichment in DCIS plasma membranes.
Figure 4B:
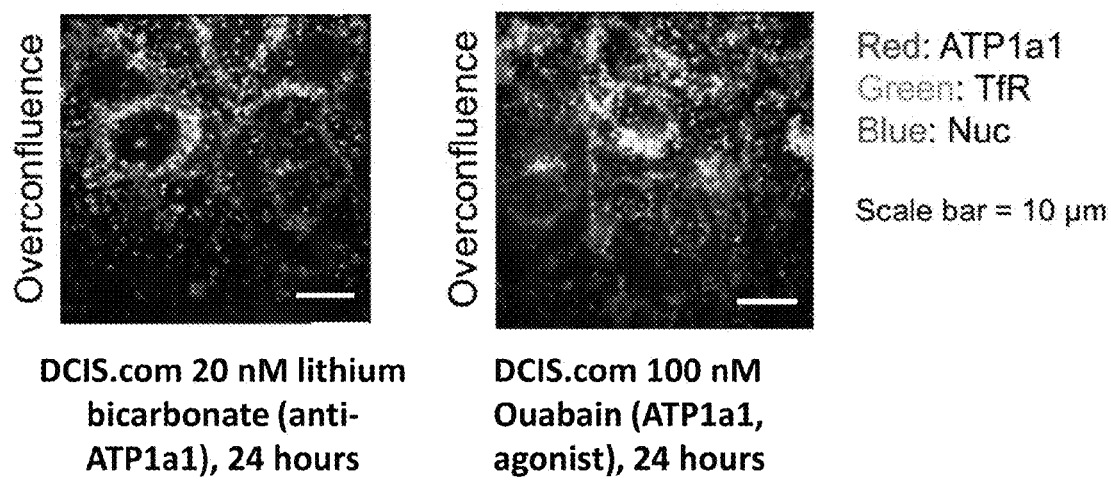
Figure 7A:
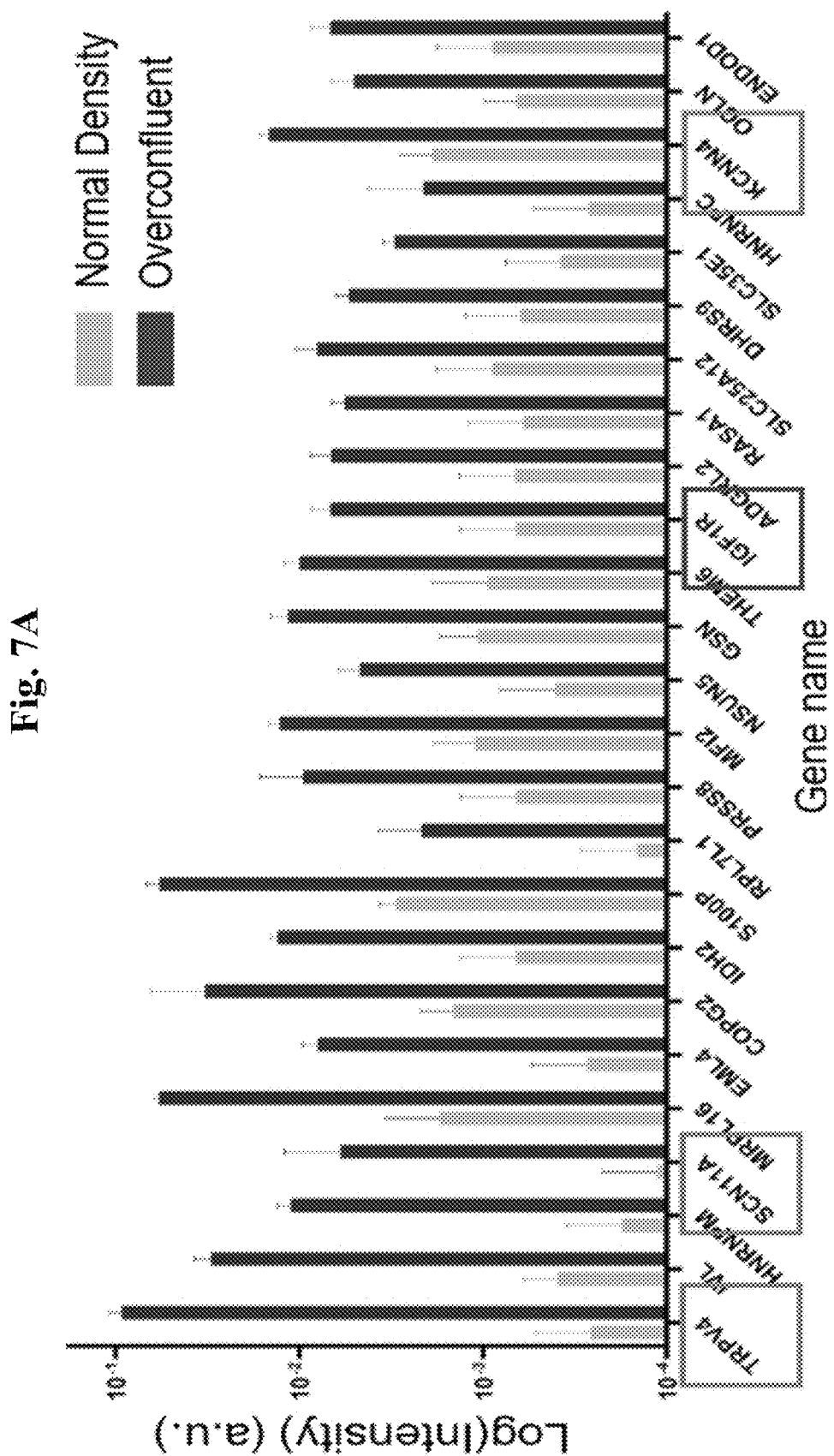

Crowding-induced cell volume changes typically occur under isotonic conditions and are accompanied by the efflux of intracellular osmolytes through ion channels. Methods herein assessed if ion channel activities were altered when cells are crowded. In general, results showed that crowding-induced enrichment of ion channels at the plasma membrane (PM) enabled ion channel to increase the efflux of free ions and further lower their volume. Ion channels showing the greatest enrichment upon crowding were TRPV4 (transient receptor potential vallinoid type and ATP1A1 (Na+/K+ transporting subunit alpha 1) (FIG. 7A). FIG. 4A shows that that TRPV4 (FIG. 4A) and ATP1A1 (FIG. 4A) were relocalized in the PM of DCIS.com cells but not in 10A and AT1 cells. Importantly, the protein enrichment did not result from increased protein expression (FIG. 7C) but from trafficking changes. These data suggested that cell-surface ion channel enrichment in crowded high-grade DCIS cells may enable cell invasion through further cell volume reduction. Additionally, when ion channel agonists (ouabain) were applied to the cell, the PM abundance of ion channels was perturbed while with antagonists (lithium bicarbonate), the perturbation was less obvious (FIG. 4B).

Example 3

Figure 5A:
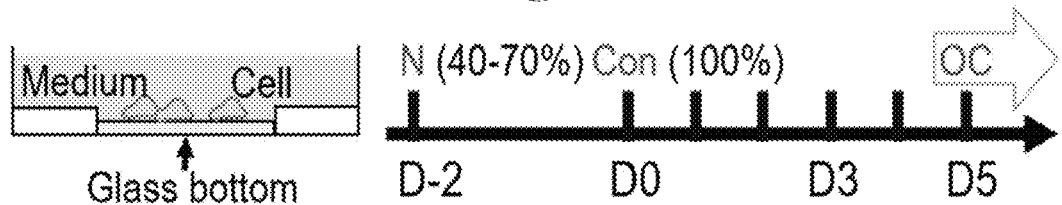
FIGS. 5A-5C depict images and graphs illustrating cell stiffening and cell volume in DCIS cells.
Figure 5B:
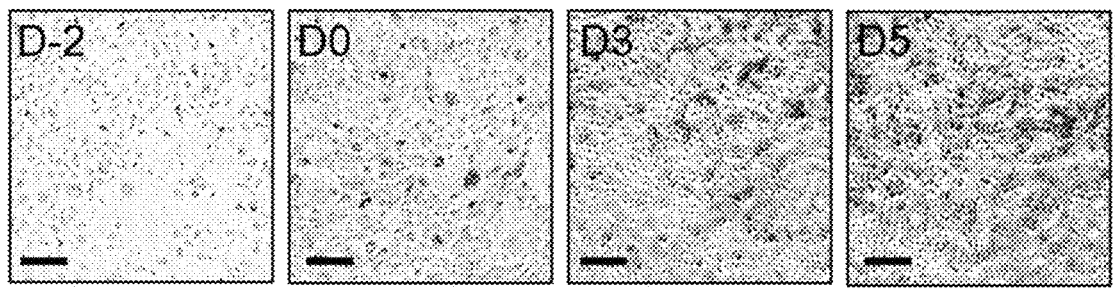
Figure 5C:
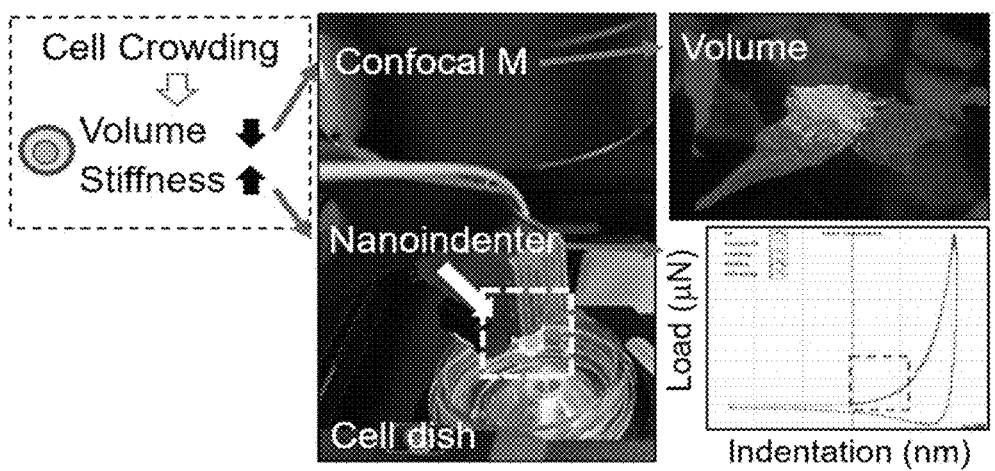

To build robust statistics about how cell crowding alters cell biomechanics in DCIS cells, exemplary methods herein measured and compared the stiffness and volume of live cells growing at normal densities (N; 40-70%) versus those that were "over" confluent [i.e., 5-7 days after cells have become confluent, to ensure equilibration of confluent cells in the crowd to mimic the confined DCIS cells in the intraductal space] (FIG. 5A). FIG. 5B shows that overall two-dimensional cell morphologies were stable for five days after reaching initial confluence. Individual cell volumes were measured using confocal microscopy of cells stably expressing RFP (FIG. 5C). Cortical stiffness of a single live cell was also measured using a nanoindenter device installed in a confocal microscope. This allowed for measurement the elastic moduli of cell surfaces (FIG. 5C) and enabled performance of light microscopy of the same cells that were being indented.

To ensure that cell volume and stiffness changes induced by cell crowding were inversely related and these biomechanical changes alter protein trafficking, the external osmotic pressure was manipulated to artificially change cell volumes and assess effects on cell stiffness and biological properties. Results showed that osmotic compression of cells with polyethylene glycol (PEG) increased Young's modulus of cells (i.e., increased stiffness) and altered protein trafficking (FIG. 10A-10D). These results indicated the altered protein trafficking results from biomechanical changes in the cell were induced by crowding.

Example 4

To compare the invasive potential of live cells between different treatment groups, exemplary methods herein established a hydrogel matrix-based invasion assay (FIG. 6A). This assay was used to quantify the invasive cell fraction as a percentage of the total, based on fluorescence imaging results (FIGS. 6B-6E). Since cell stiffness is modulated by the stiffness of the surroundings [the values for normal breast versus DCIS cells are known to be ~0.1 versus ~10 kPa], the hydrogel matrix could be stiffness-controlled within the range specified above, as confirmed by nanoindenter measurements. Using the hydrogel matrix-based invasion assay described herein, external stiffness changes were observed to be insufficient to elicit protein trafficking changes in normal-density DCIS.com cells (FIGS. 6F-6G), suggesting that cell crowding effects outweigh external stiffness variations.

Figure 11C:
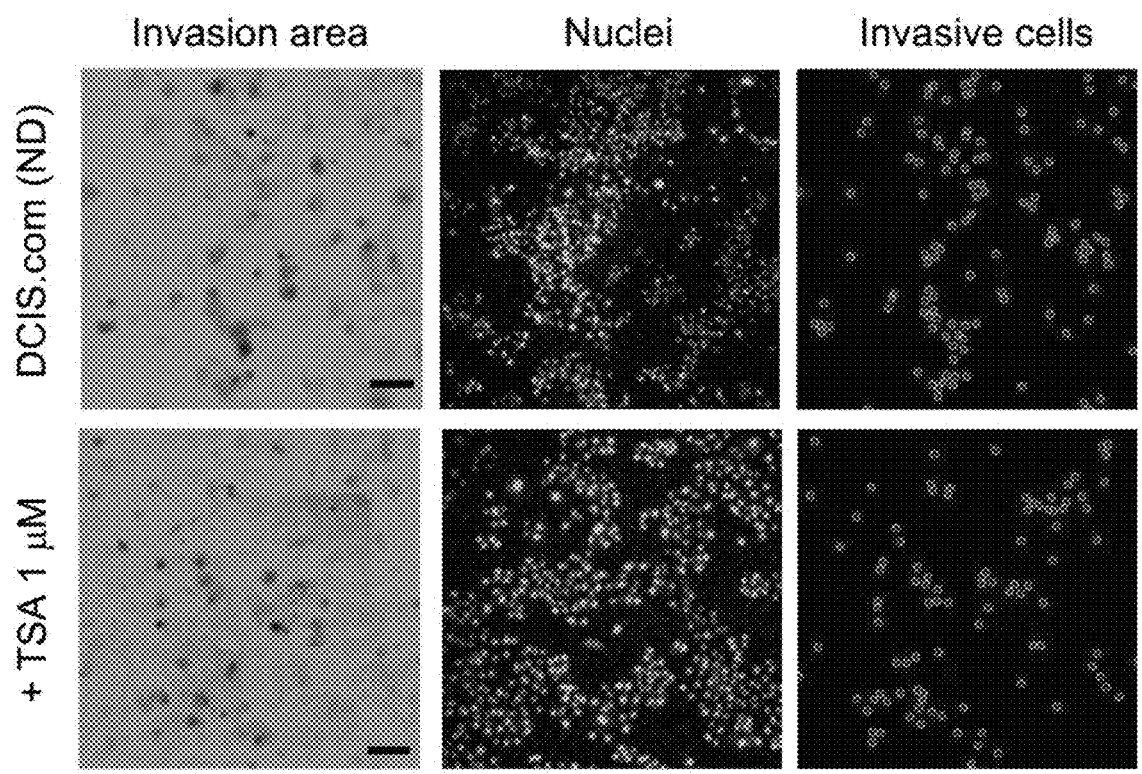
Figure 11D:
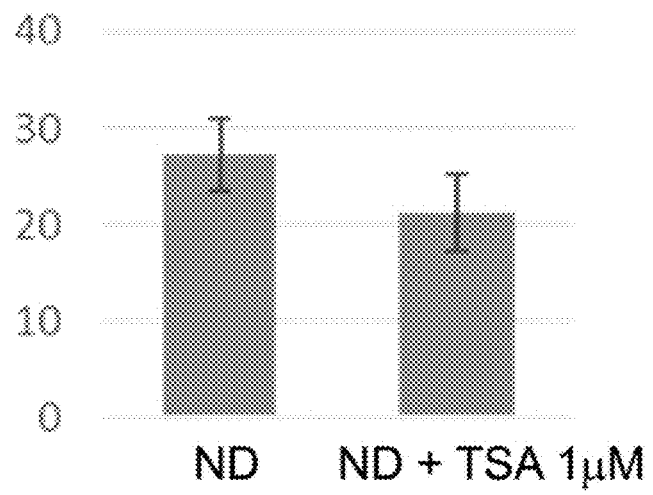

Also assessed were two independent possibilities for crowding-mediated increased invasiveness: YAP-association and cell cycle arrest (high-density cells are subject to G1 arrest). YAP mRNA was reduced when DCIS.com cells were overconfluent (OC) versus normal (N) density (FIG. 11A), and all six tested cell lines exhibited similar G1 arrest. Treating crowded cells with a cell cycle inhibitor (Trichostatin A; TSA) reversed the cell cycle arrest (FIG. 11B) but did not decrease the invasiveness of DCIS.com cells (FIGS. 11C-11D). Therefore, these two possibilities did not account for the increased invasiveness of DCIS.com cells.

Example 5

Exemplary methods herein subjected DCIS.com cells to mass spectrometry (MS) experiments. MS studies of DCIS-.com cells showed that ion channels and other proteins translocated to the PM during cell crowding (FIG. 7A). DCIS.com cells showed crowding-induced plasma membrane (PM) enrichment of ion channels, including TRPV4, KCNN4, SCN11A (#1 MS result), and ATP1A1 (#2 MS result). Ion channels showing the greatest enrichment upon crowding were TRPV4 (transient receptor potential vallinoid type 4) and ATP1A1 (Na+/K+ transporting subunit alpha 1). These data implied a linkage between cell crowding-induced volume reduction (or increased cell stiffness) and altered protein trafficking. PEG-treated DCIS.com cells showed significant enrichment of ion channels on the PM; other proteins, such as transferrin receptors, were not affected by osmotic compression (FIGS. 10A-10D).

MS results showed that growth factor (GF) receptors such as IGFR1 (purple box in FIG. 7A) were also elevated on the surfaces of OC DCIS.com cells. Exemplary methods using IGFR1 inhibitors or RNAi are used in cell lines herein to assess whether increased GF signaling contributes to cell-crowding-induced cell invasion.

Three sequential approaches are used to assess relative protein levels on the cell surface: 1) MS on surface-biotinylated cell lysates from N densities versus OC, 2) immunoblot of surface-biotinylated cell lysates, and 3) confocal and super-resolution structured illumination microscopy (SIM) imaging to illuminate the locations of proteins in different subcellular regions, using a custom-built super-resolution microscope that doubles optical resolution in all three dimensions. Data herein demonstrated the feasibility of this three-step scheme for analysis of patient-derived primary cells. MS data using the DCIS.com cell line revealed PM enrichment of ion channels (FIG. 7A) when DCIS.com cells were grown OC versus at N densities. Immunoblot data on TRPV4 showed similar PM protein enrichment when DCIS.com cells are grown OC (FIG. 7B), yet their overall protein levels were similar to cells grown at N density (FIG. 7C). The confocal and 3D SIM data revealed PM enrichment of TRPV4 in OC DCIS.com cells, while at normal density, TRPV4s were found in the cytosol associated with intracellular organelles such as golgi (FIG. 7D).

To determine the effects of ion-channel-activity-dependent cell volume variability on cell invasiveness, cell volume variability is defined as the extent of volume reduction in cells as they go from N density to OC conditions. The extent to which a cell can reduce its volume upon crowding reflects the cell's adaptability to its surrounding, which is crucial for invasiveness. How inhibition and over-activation of TRPV4, ATP1A1, KCNN4, and SCN11A affects cell volume variability is determined by measuring volumes at N and OC densities, with and without blocking ion channel activity by siRNA and/or specific inhibitors (e.g., GSK2193874 as a TRPV4 inhibitor). Volume changes are assessed using confocal microscopy and 3D-SIM as described herein. PEG treatment is used to maximally reduce cell volume to determine the limit of ion channel-dependent cell volume reduction. ATP1A1 agonist or inhibitor in DCIS.com affects cell volume variability and whether ion channel inhibition de-localizes PM ATP1A1 to the cytosol (FIG. 4B) are examined to support the importance of PM-enriched ATP1A1 in modulating cell volume.

The two independent MS experiments disclosed herein (FIG. 7A) showed that TRPV4 and ATP1A1 were the most elevated ion channels on the PM induced by cell crowding in DCIS.com cells. However, their protein expression levels were comparable to what was seen in more benign (10A and AT1) or invasive (CA1a) analogs. Using a panel of patient tissue sections and breast/glioma cell lines, significance of TRPV4 and ATP1A1 is determined by RNAseq and in vitro tests according to the exemplary methods disclosed herein.

Example 6

Exemplary methods herein determine the ranges of stiffness and cell volume values of all four 10A derivatives at N density, and the extent of cell volume changes at OC density. The resulting stiffness and cell volume values are linked to TRPV4 localization to the PM by artificially modulating the cell volume through external osmotic pressure using PEG. Similar experiments are repeated on patient-derived primary high-grade DCIS cells at N and OC densities, determining how ranges obtained from DCIS.com cells relate to clinical invasive potential.

Vimentin and keratin expressions and cellular arrangements are correlated with cell stiffness variation and cell invasion. Vimentin and keratin expression levels and arrangements in N and OC densities, high-grade DCIS cells are assessed and effects on cell volume variability and initial volume are determined.

Example 7

Figure 8A:
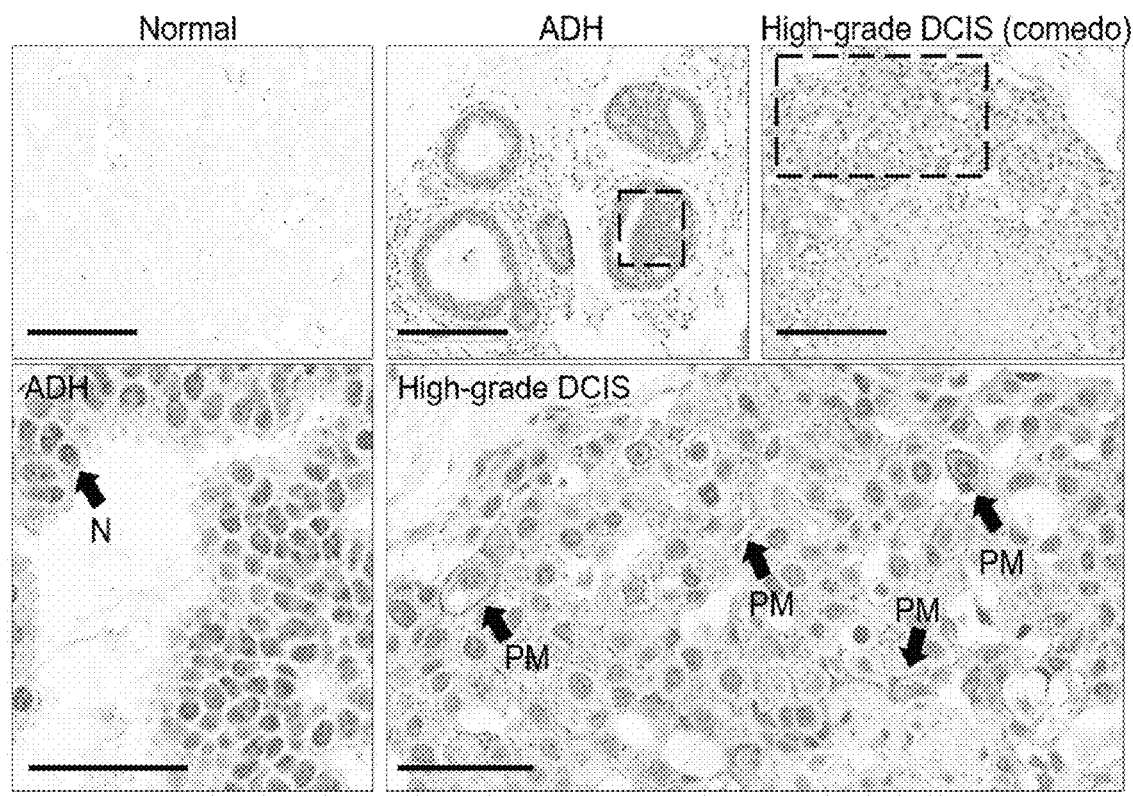
FIGS. 8A-8B depict images of human breast tissue samples and cells.
Figure 8B:
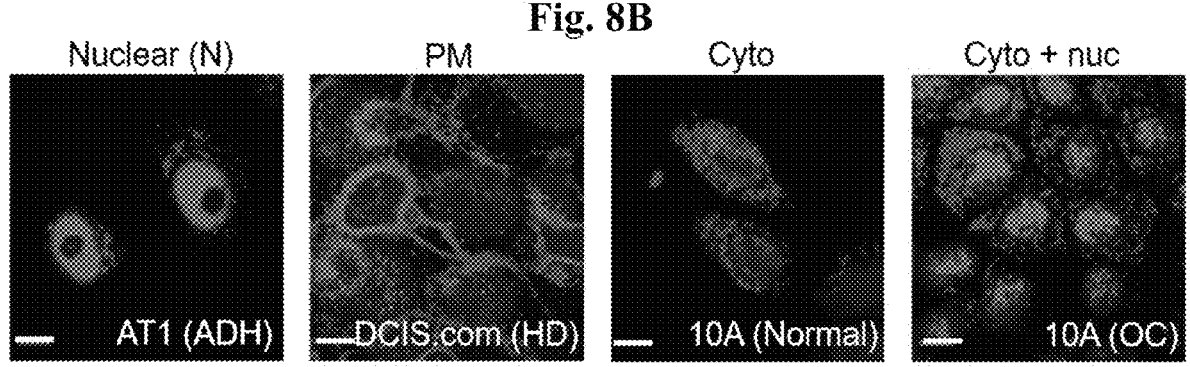
Figure 9A:
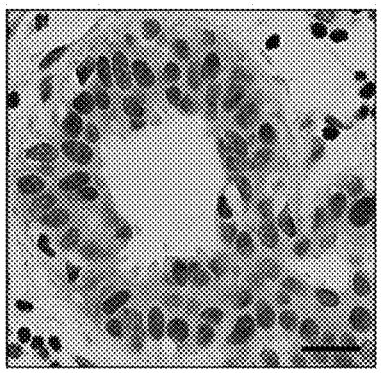
FIGS. 9A-9F depict images of human breast tissue samples. Immunohistochemistry (IHC) was performed and images show TRPV4 staining of normal (FIG. 9A), benign (FIG. 9B), ADH (FIG. 9C), IMG-DCIS (FIG. 9D), HG-DCIS (FIG. 9E), and IDC (FIG. 9F) breast tissue samples.
Figure 9B:
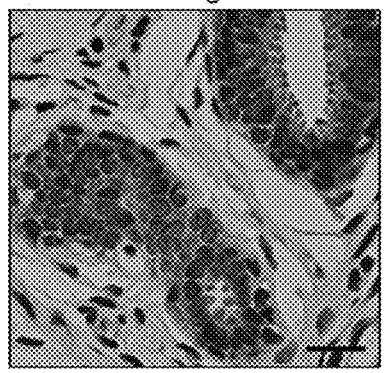
Figure 9C:
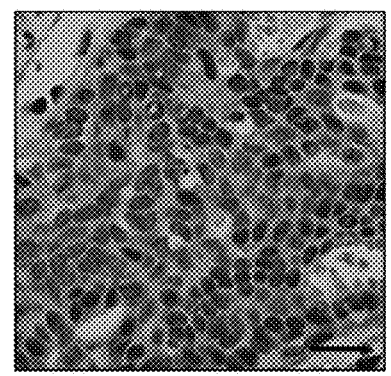
Figure 9D:
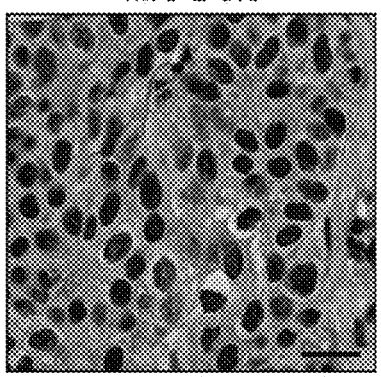
Figure 9E:
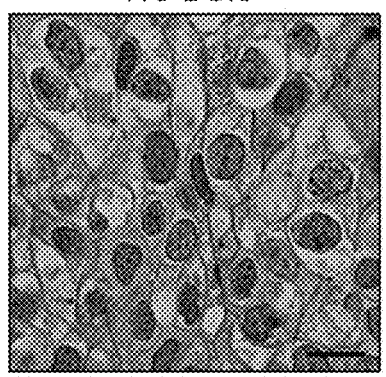
Figure 9F:
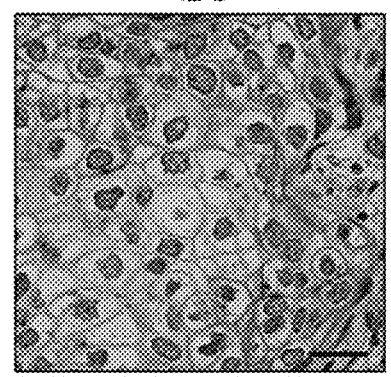

Exemplary methods herein verified that TRPV4 was PM-enriched in the patient-derived high-grade DCIS and IDC cells, as observed in the cell lines (FIG. 7B). In brief, a retrospective clinical study was designed where breast tissue specimens that feature all four pathologies (ADH, low- and high-grade DCIS, and IDC) along with normal tissue were selected for each patient. Specimens associated with a past cancer diagnosis and drug treatment history were be excluded. Initial analyses included IHC imaging for differential ion channel distributions between different pathologies within a specimen. FIG. 8A shows selective cell-surface enrichment of TRPV4 in high-grade DCIS, but not in ADH or normal regions and illustrate the potential of PM TRPV4 as a diagnostic marker. Other correlations with other disease conditions (e.g., cholesterol-mediated disorders like heart diseases that may affect PM protein compositions) where TRPV4 or other ion channels are significantly related to disease severity are considered. The correlation of TRPV4 localization patterns (FIGS. 8A-8B) with the disease state (from pathology reports) is also examined.

Gene expression profiles of ion channels in patient samples are assed in the patient cells with various disease stages (Table 1) using FFPE (Formalin-Fixed Paraffin-Embedded) sections. Although a noticeable difference in protein expression levels of ion channels such as TRPV4 and ATP1A1 was not observed between the four 10A derivatives, negative staining of TRPV4 was seen in normal breast sections by IHC. The threshold expression level that enables crowded DCIS cells to become invasive is determined and ion channels are profiled. Those in high-grade DCIS samples may be important in cell-crowding induced altered biomechanics, ion channel trafficking, and increased invasion.

Example 8

Exemplary methods examined the clinical significance of the correlation of PM residence of TRPV4 at the PM with HG DCIS and IDC phenotypes using a retrospective clinical study to select breast tissue specimens that feature any of the five pathologies (benign: usual ductal hyperplasia, papilloma, or columnar, ADH, low-intermediate grade DCIS, high-grade DCIS, and IDC: intermediate or high-grade) along with normal tissue for each patient. Specimens associated with a past cancer diagnosis and drug treatment history were excluded. A total of 98 regions of interest (ROI) were selected from the hematoxylin and eosin (H&E) stained images obtained from 47 patient tissue blocks. Two pathologists evaluated each ROI independently in the corresponding IHC images for the PM presence of TRPV4 at a single-cell level (FIGS. 9A-9F and Table 2).

volume modulation for cell invasion by HG-DCIS and IDC cells. In benign or normal breast epithelial cells, TRPV4 staining was still present mostly in the nuclei, implying the significance of protein relocation phenotypes, rather than expression levels, in differentiating different disease phenotypes. These data confirm the in-vitro findings described in the exemplary methods herein, revealing the highly selective PM presence of TRPV4 in mostly HG-DCIS or IDC, rather than in LG/IM-DCIS, ADH, or benign regions, illustrating the potential of high-fidelity diagnostic/prognostic utilities of PM TRPV4 in IHC examinations.

All the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of detecting ductal carcinoma in situ (DCIS) at risk of disease progression in a subject, the method comprising:
   detecting in a tissue sample obtained from a subject diagnosed with DCIS the presence of one or more ion channels localized (i) at the plasma membrane in one or more cells of the tissue sample and (ii) in the cytoplasm and/or the nucleus of the one or more cells of the tissue sample; and

TABLE 2

| | \multicolumn{18}{c|}{Breast pathology duct phenotypes} |
|---|---|---|---|---|---|---|---|---|---|---|---|---|---|---|---|---|---|---|
| | Normal | | | Benign | | | ADH | | | LG/IM-DCIS | | | HG-DCIS | | | IDC | | |
| Total number of ROIs | 14 | | | 32 | | | 9 | | | 7 | | | 20 | | | 17 | | |
| | Y | N | E | Y | N | E | Y | N | E | Y | N | E | Y | N | E | Y | N | E |
| Number of ROIs featuring PM TRPV4 | 0 | 14 | 0 | 0 | 4 | 0 | 0 | 9 | 0 | 0 | 6 | 1 | 15 | 1 | 4 | 17 | 0 | 0 |
| Proportion (%) of ROIs featuring PM TRPV4 | 0 | | | 0 | | | 0 | | | 0 | | | 75% | | | 73% | | |

Table 2 summarizes the evaluation for the PM residence of TRPV4 in all six breast pathology phenotypes. For instance, out of 20 HG-DCIS ROIs, PM TRPV4 was confirmed (Y) in 15 ROIs, while 4 ROIs were equivocal (E) and 1 ROI did not show a clear PM staining (N). The sensitivity and specificity of these tests for PM TRPV4 positivity in HG-DCIS were 0.75 and 0.98, a 95% confidence interval of 0.75±0.19, 0.98±0.03, respectively. PM TRPV4 was also frequently observed in IDC, similarly to HG-DCIS, while PM TRPV4 was absent in the ROIs associated with less severe pathologies. These results were indicative of the selective and frequent utilization of ion-channel-based cell identifying the DCIS as having a high likelihood of becoming an invasive DCIS or an invasive breast cancer when the one or more ion channels are enriched at the plasma membrane, or identifying the DCIS as having a low likelihood of becoming an invasive DCIS or an invasive breast cancer when the one or more ion channels are not enriched at the plasma membrane; and using the identification of the DCIS as having a high likelihood of becoming invasive DCIS or an invasive breast cancer to treat the subject, wherein treating comprises administering to the subject chemotherapy, radiation, and/or a targeted therapy, surgically removing breast tissue from the subject, or a combination thereof.

2. The method of claim 1, wherein the one or more ion channels is ATP1A1.

3. The method of claim 1, further comprising: obtaining the tissue sample from the subject.

4. The method of claim 1, wherein detecting the presence of the one or more ion channels localized at the plasma membrane in the one or more cells of the tissue sample comprises detecting the presence of at least two ion channels localized at the plasma membrane in the one or more cells of the tissue sample.

5. The method of claim 1, further comprising calculating an invasiveness risk score
   (i) by quantifying in the tissue sample the fraction of DCIS cells that have the presence of the one or more ion channels enriched at the plasma membrane, or
   (ii) by quantitatively assessing in the tissue sample the level of the one or more ion channels enriched at the plasma membrane in each positive DCIS cell,
   wherein a higher fraction or higher level correlates with a high invasiveness risk score.

6. The method of claim 5, wherein the quantitatively assessing the level of the one or more ion channels enriched at the plasma membrane in each positive DCIS cell comprises using a multivariate prediction model to determine whether a pattern of plasma membrane localization of the one or more ion channels is indicative of DCIS having a high likelihood of becoming invasive.

7. The method of claim 3, wherein the tissue sample is a breast tissue sample.

8. The method of claim 1, wherein detecting the presence of the one or more ion channels localized at the plasma membrane, in the cytoplasm, and/or in the nucleus comprises using immunohistochemistry, immunocytochemistry, or flow cytometry.

9. The method of claim 1, wherein detecting the presence of the one or more ion channels localized at the plasma membrane, in the cytoplasm, and/or in the nucleus comprises using antibodies or antibody fragments having binding specificity for the one or more ion channels.

10. The method of claim 9, wherein the antibodies or antibody fragments comprise a detectable label, and wherein the detectable label comprises a fluorescent marker, an enzyme, a small molecule, a contrast agent, or a second antibody.

11. The method of claim 1, further comprising confirming the presence of one or more ion channels localized at the plasma membrane by colocalization with at least one invariant control marker present at the plasma membrane.

12. The method of claim 11, wherein the at least one invariant control marker is the transferrin receptor.

13. The method of claim 1, wherein prior to the detecting step, the subject had been diagnosed with DCIS by calcification detected by mammography.

14. The method of claim 1, further comprising comparing the level of detection of the one or more ion channels at the plasma membrane to the level of detection of the one or more ion channels in the cytoplasm and/or in the nucleus.

15. The method of claim 1, further comprising confirming the presence of one or more ion channels localized in the cytoplasm and/or the nucleus by colocalization with an invariant control marker present in the cytoplasm and/or the nucleus.

16. A method of treating a subject having ductal carcinoma in situ (DCIS) at risk of disease progression, the method comprising:
    identifying the DCIS as having a high likelihood of becoming an invasive DCIS or an invasive breast cancer by detecting in a tissue sample obtained from a subject the enrichment of one or more ion channels localized at the plasma membrane in one or more cells of the tissue sample, and
    treating the subject by administering to the subject chemotherapy, radiation, and/or a targeted therapy, surgically removing breast tissue, or any combination thereof.

17. The method according to claim 16, wherein the one or more ion channels is ATP1A1.

18. The method according to claim 16, wherein identifying the DCIS as having a high likelihood of becoming an invasive DCIS or an invasive breast cancer comprises
    detecting in a tissue sample obtained from the subject diagnosed with DCIS the presence of the one or more ion channels localized (i) at the plasma membrane in the one or more cells of the tissue sample and (ii) in the cytoplasm and/or the nucleus of the one or more cells of the tissue sample; and
    comparing the level of detection of the one or more ion channels at the plasma membrane to the level of detection of the one or more ion channels in the cytoplasm and/or in the nucleus,
    wherein when the one or more ion channels are enriched at the plasma membrane, the DCIS is identified as having a high likelihood of becoming an invasive DCIS or an invasive breast cancer.

19. The method of claim 10, wherein the second antibody comprises a detectable label, and wherein the detectable label comprises a fluorescent marker, an enzyme, a small molecule, or a contrast agent.

* * * * *